(12) United States Patent
Kuboe et al.

(10) Patent No.: US 8,455,564 B2
(45) Date of Patent: *Jun. 4, 2013

(54) DENTAL COMPOSITION AND COMPOSITE RESIN

(75) Inventors: Yoshiko Kuboe, Kurashiki (JP); Masaki Okubayashi, Kurashiki (JP); Koichi Okada, Tokyo (JP); Keisuke Ohtsuka, Kitakyushu (JP)

(73) Assignees: Kuraray Noritake Dental Inc., Kurashiki-shi (JP); JGC Catalysts and Chemicals Ltd., Kawasaki-shi (JP)

( * ) Notice: Subject to any disclaimer, the term of this patent is extended or adjusted under 35 U.S.C. 154(b) by 232 days.

This patent is subject to a terminal disclaimer.

(21) Appl. No.: 12/990,077

(22) PCT Filed: Apr. 28, 2009

(86) PCT No.: PCT/JP2009/058416
§ 371 (c)(1),
(2), (4) Date: Oct. 28, 2010

(87) PCT Pub. No.: WO2009/133912
PCT Pub. Date: Nov. 5, 2009

(65) Prior Publication Data
US 2011/0046261 A1    Feb. 24, 2011

(30) Foreign Application Priority Data
Apr. 28, 2008    (JP) .................................. 2008-117799

(51) Int. Cl.
*A61K 6/083*    (2006.01)
*A61K 6/08*    (2006.01)
*A61L 24/02*    (2006.01)

(52) U.S. Cl.
USPC .......... 523/115; 523/113; 433/228.1; 106/35; 977/919

(58) Field of Classification Search
USPC ... 523/115, 113; 433/228.1; 106/35; 977/919
See application file for complete search history.

(56) References Cited

U.S. PATENT DOCUMENTS

| 4,719,297 A | 1/1988 | Henne et al. |
| 5,055,497 A | 10/1991 | Okada et al. |

(Continued)

FOREIGN PATENT DOCUMENTS

| EP | 0 009 348 | 4/1980 |
| JP | 57 197289 | 12/1982 |

(Continued)

OTHER PUBLICATIONS

English machine translation of JP 2006052128 A; Aug. 9, 2012.*

(Continued)

*Primary Examiner* — Michael Pepitone
(74) *Attorney, Agent, or Firm* — Oblon, Spivak, McClelland, Maier & Neustadt, L.L.P.

(57) ABSTRACT

A dental composition of the present invention includes: a polymerizable monomer component (A); and an amorphous filler (B) having an average particle size of 1 to 20 μm and including silica-based fine particles and coatings of an oxide that cover the surfaces of the silica-based fine particles. The oxide contains a zirconium atom, a silicon atom, and an oxygen atom. The dental composition contains 20 to 500 parts by weight of the filler (B) per 100 parts by weight of the polymerizable monomer component (A). The dental composition has a viscosity of 10 to 800 Pa·s. It is preferable that the filler (B) contain spherical particles, and that the percentage of the spherical particles in the filler (B) be at least 60%.

20 Claims, 2 Drawing Sheets

U.S. PATENT DOCUMENTS

| | | | |
|---|---|---|---|
| 5,192,815 | A | 3/1993 | Okada et al. |
| 5,795,497 | A | 8/1998 | Kimura et al. |
| 6,849,112 | B2 | 2/2005 | Nishida et al. |
| 6,849,670 | B2 | 2/2005 | Satoh et al. |
| 6,933,327 | B2 * | 8/2005 | Yamakawa et al. ............ 523/115 |
| 7,981,513 | B2 * | 7/2011 | Ohtsuka et al. ............... 428/403 |
| 2002/0022677 | A1 | 2/2002 | Teramae et al. |
| 2002/0115042 | A1 | 8/2002 | Hasel |
| 2004/0151691 | A1 | 8/2004 | Oxman et al. |
| 2005/0113480 | A1 | 5/2005 | Usuki et al. |
| 2007/0207094 | A1 | 9/2007 | Oxman et al. |
| 2009/0253825 | A1 | 10/2009 | Ohtsuka et al. |
| 2010/0056664 | A1 | 3/2010 | Ohtsuka et al. |

FOREIGN PATENT DOCUMENTS

| | | | |
|---|---|---|---|
| JP | 63 088110 | | 4/1988 |
| JP | 2 028204 | | 1/1990 |
| JP | 2 134307 | | 5/1990 |
| JP | 6 107516 | | 4/1994 |
| JP | 9 169613 | | 6/1997 |
| JP | 9 255516 | | 9/1997 |
| JP | 10 001473 | | 1/1998 |
| JP | 11 092461 | | 4/1999 |
| JP | 2000 159621 | | 6/2000 |
| JP | 2001 139411 | | 5/2001 |
| JP | 2001 302429 | | 10/2001 |
| JP | 2002 138008 | | 5/2002 |
| JP | 2002 204803 | | 7/2002 |
| JP | 2003 146822 | | 5/2003 |
| JP | 3421072 | | 6/2003 |
| JP | 2005 154312 | | 6/2005 |
| JP | 2006 52128 | | 2/2006 |
| JP | 2006052128 A | * | 2/2006 |
| JP | 2006 516544 | | 7/2006 |
| JP | 2007 261967 | | 10/2007 |
| WO | 02 05752 | | 1/2002 |
| WO | 2007 111066 | | 10/2007 |
| WO | 2008 056485 | | 5/2008 |
| WO | WO 2008/056485 A1 | * | 5/2008 |

OTHER PUBLICATIONS

International Search Report issued Jul. 28, 2009 in PCT/JP09/058416 filed Apr. 28, 2009.
U.S. Appl. No. 12/989,962, filed Oct. 28, 2010, Okubayashi, et al.
U.S. Appl. No. 12/989,996, filed Oct. 28, 2010, Okubayashi, et al.
Extended European Search Report issued Dec. 23, 2011, in European Patent Application No. 09738849.0.

* cited by examiner

DENTAL COMPOSITION AND COMPOSITE RESIN

CROSS-REFERENCE TO RELATED APPLICATIONS

This application is a 371 of PCT/JP2009/058416 filed Apr. 28, 2009. Priority to Japan 2008-117799, filed Apr. 28, 2008, is claimed.

TECHNICAL FIELD

The present invention relates to a dental composition that can be used as a substitute for a part of a natural tooth or an entire natural tooth in the field of dental treatment, and to a composite resin using the dental composition.

BACKGROUND ART

A dental composition contains a polymerizable monomer, a polymerization initiator, and an inorganic filler, and is most widely used today as a restorative material for repairing fractures of teeth and dental caries. Such a dental composition is required to have the following properties. Specifically, as a cured product obtained after polymerization, the dental composition is required to have sufficient mechanical strength and hardness to serve as a substitute for natural teeth, wear resistance against occlusion of teeth in an oral cavity, surface smoothness and gloss, color matching with natural teeth, transparency, etc. Furthermore, from the viewpoint of handling properties, the dental composition, as a paste which has not yet been polymerized, is desired to have ease of handling for dental clinicians, for example, proper fluidity and high forming property. Particularly, a type of composition to be filled directly in a cavity must have a viscosity low enough to be filled directly from a syringe. If a specific component is added or the blend ratio of the components is adjusted, the resulting composition can produce favorable effects as a dental material.

These properties of the dental composition are greatly influenced by the component materials, shape, particle size of an inorganic filler used therein, and further by the content of that filler. For example, when an inorganic filler having a large average particle size of 1 μm or more is used, the filling rate of the filler in the polymerizable monomer can be increased easily and therefore sufficient mechanical strength as a cured product and high handling properties as a paste can be obtained. The use of such an inorganic filler has, however, a drawback in that it is difficult to obtain satisfactory gloss even after final polishing. On the other hand, when an inorganic ultrafine particle filler having an average particle size of less than 1 μm is used, the surface smoothness and gloss after polishing of the cured product and the gloss durability in the oral cavity are improved. The use of such an inorganic ultrafine particle filler has, however, a drawback in that when the inorganic filler is mixed and kneaded with the polymerizable monomer, the viscosity of the resulting paste increases significantly, which makes it difficult to increase the content of the filler. As a result, the mechanical strength of the cured product decreases, and the unpolymerized pasty composition becomes sticky, which reduces the handling properties. When a conventional dental composition, particularly a type of composition to be filled directly in a tooth is used, a reduction in the content of an inorganic filler seems to be a good solution to meet the handling properties requirements. However, when the content of the inorganic filler is reduced, the physical properties such as flexural strength of the resulting composition are low in value. When the content of the inorganic filler is increased to increase the strength, the viscosity of the resulting composition also increases. Such a composition cannot be used for direct filling during dental treatment. Furthermore, a spherical filler can be used to increase the surface smoothness and gloss, but it is difficult to increase the strength while maintaining the handling properties. Under these circumstances, it is difficult to increase the mechanical strength and the surface smoothness and gloss after polishing of the cured product and the handling properties of the paste in a balanced manner.

Patent Literature 1 discloses a dental restorative material in which an inorganic filler treated with a specific silane coupling agent and a polymerizable monomer having high hydrophobicity are used in combination to achieve high density filling, high strength, high aesthetic quality, and durability. In a dental restorative material disclosed in Patent Literature 2, a mixed filler composed of irregular-shaped inorganic particles, spherical inorganic particles, and inorganic ultrafine particles are used. The irregular-shaped particles having a small average particle size are used in this mixed filler, and acylphosphine oxide is used as a photopolymerization catalyst, so that the resulting dental restorative material has increased surface smoothness and gloss while maintaining high fracture toughness and strength. Patent Literature 3 discloses a dental composition in which a spherical filler having a specific particle size is used to achieve a good balance between the paste properties and the polishability.

CITATION LIST

Patent Literature

Patent Literature 1 JP 02(1990)-134307 A
Patent Literature 2 WO 2002/05752 A1
Patent Literature 3 JP 2001-139411 A

SUMMARY OF INVENTION

Technical Problem

However, despite the above attempts to obtain a suitable combination between an inorganic filler and other components, it is difficult to increase the strength of the dental composition, improve the surface smoothness and gloss, and further achieve a good balance between these properties and the handling properties, particularly the handling properties as a direct-filling material.

It is an object of the present invention to provide a dental composition exhibiting excellent mechanical strength, surface smoothness and gloss after polishing as a cured product, and excellent handling properties as a paste.

Solution to Problem

The present inventors have conducted intensive studies to solve the above-mentioned problems. As a result, the inventors have found that the content of an inorganic filler can be increased by adding a specified amount of filler having a specific structure and a specific particle size range and the resulting dental composition has excellent surface smoothness and gloss after polishing and excellent paste handling properties while maintaining high strength, and have achieved the present invention.

The dental composition of the present invention includes: a polymerizable monomer component (A); and an amorphous filler (B) having an average particle size of 1 to 20 μm and including silica-based fine particles and coatings of an oxide that cover the surfaces of the silica-based fine particles. The oxide contains a zirconium atom, a silicon atom, and an oxygen atom. This dental composition contains 20 to 500 parts by weight of the filler (B) per 100 parts by weight of the polymerizable monomer component (A), and has a viscosity of 10 to 800 Pa·s.

The present invention also provides a composite resin using the dental composition of the present invention.

Advantageous Effects of Invention

The dental composition of the present invention contains the specified amount of the filler (B) having the above specific structure and specific particle size range, and produces advantageous effects of providing excellent surface smoothness and gloss after polishing and excellent paste handling properties while maintaining high strength.

DESCRIPTION OF EMBODIMENTS

Figure 1:
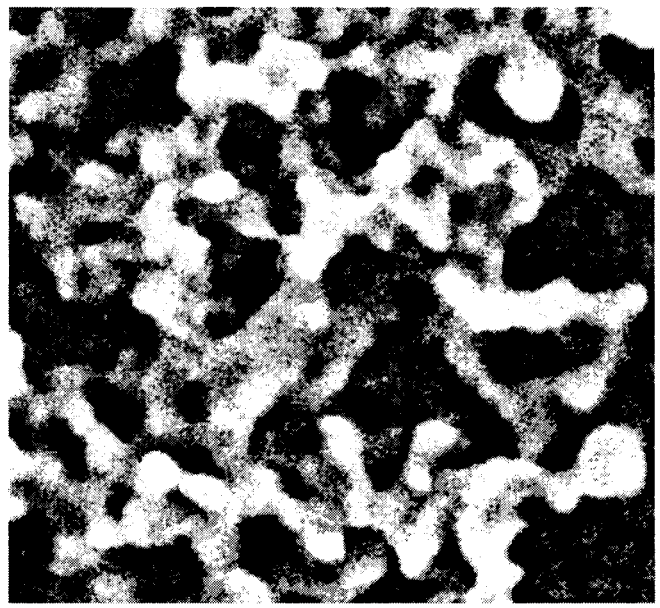
FIG. 1 is an SEM micrograph (×500000) of one example of an amorphous filler (B) which has been subjected to a drying process.

The dental composition of the present invention includes: a polymerizable monomer component (A); and an amorphous filler (B) having an average particle size of 1 to 20 μm and including silica-based fine particles and coatings of an oxide that cover the surfaces of the silica-based fine particles. The oxide contains a zirconium atom, a silicon atom, and an oxygen atom. The dental composition of the present invention contains 20 to 500 parts by weight of the filler (B) per 100 parts by weight of the polymerizable monomer component (A). Furthermore, the dental composition of the present invention has a viscosity of 10 to 800 Pa·s.

When a tooth is restored using a conventional dental composition, the composition in a container cannot be filled directly in a dental cavity because it has a high viscosity. Instead, the following procedure is generally used. An appropriate amount of the composition is taken out of the container by a dental filling tool such as a dental instrument, and then filled in the cavity, shaped to conform to the shape of the cavity, and cured.

The dental composition of the present invention has a low viscosity, and has an appropriate degree of forming property. Therefore, the composition can be dispensed from a container (a syringe-type container) through a nozzle mounted at the tip of the container and having a diameter smaller than a dental cavity. Thus, the composition can be filled in the cavity directly from the syringe. In addition, since the composition only needs to be poured into the cavity to be filled therein, the treatment time can be reduced. In the present description, a type of treatment material to be filled in a cavity, etc. directly from a container of a dental composition in the manner as described above is referred to as a direct-filling treatment material.

The dental composition of the present invention contains a filler having an average particle size of 1 to 20 μm and including silica-based fine particles and coatings of an oxide that cover the surfaces of the silica-based fine particles. The oxide contains a zirconium atom, a silicon atom, and an oxygen atom. Preferably, in this filler, the number of particles having a particle size of 0.5 μm or less is 10% or less and the number of particles having a particle size of 30 μm or more is 10% or less. Accordingly, the content of the filler can be increased. As a result, the dental composition of the present invention can produce advantageous effects of providing excellent surface smoothness and gloss after polishing and excellent paste handling properties while maintaining high strength. Hereinafter, the essential components of the present invention are described.

As the polymerizable monomer component (A) used in the present invention, a known polymerizable monomer used for dental compositions can be used without any limitation. For example, polymerizable monomers including an aromatic polymerizable monomer (a) having a hydroxyl group, an aromatic polymerizable monomer (b) not having a hydroxyl group, and an aliphatic polymerizable monomer (c) can be used preferably.

In the present invention, a "polymerizable monomer" means a compound having at least one polymerizable group. Generally in dental compositions, radical polymerization is performed. Therefore, the polymerizable group is typically a radical polymerizable group. As the polymerizable group, a (meth)acryloyloxy group, or a (meth)acryloylamino group is preferable. From the viewpoint of availability, a (meth)acryloyloxy group is more preferable. From the viewpoint of safety to living bodies, a methacryloyloxy group is further preferable.

In the present invention, an "aromatic polymerizable monomer" means a polymerizable monomer having at least one aromatic ring. The aromatic ring may be any of a benzene ring, a fused benzene ring (such as naphthalene), a nonbenzenoid aromatic ring, and a heteroaromatic ring (such as a pyridine ring or a pyrrole ring). Preferably, the aromatic ring is a benzene ring.

In the present invention, an "aliphatic polymerizable monomer" means a polymerizable monomer not having an aromatic ring.

The aromatic polymerizable monomer (a) having a hydroxyl group is a polymerizable monomer having at least one hydroxyl group, at least one aromatic ring, and at least one polymerizable group. The numbers of hydroxyl groups, aromatic rings, and polymerizable groups are not particularly limited. From the viewpoints of the availability and the mechanical strength as a cured product of the dental composition, the number of polymerizable groups is preferably 1 to 6, and more preferably 2 to 4. From the viewpoints of the availability and the hydrophilicity of the dental composition, the number of hydroxyl groups is preferably 1 to 3. From the viewpoints of the availability and the mechanical strength as a cured product of the dental composition, the number of aromatic rings is preferably 1 to 3, and more preferably 2. It is particularly preferable that the polymerizable monomer (a) has a structure of a bisphenol A skeleton (i.e., a structure in which hydrogen atoms are removed from two hydroxyl groups in bisphenol A). Examples of such a polymerizable monomer (a) include 2,2-bis[4-[3-(meth)acryloyloxy-2-hydroxypropoxy]phenyl]propane (hereinafter sometimes referred to as "Bis-GMA"), 2-[4-[3-(meth)acryloyloxy-2-hydroxypropoxy]phenyl]-2-[4-[2,3-di(meth)acryloyloxy propoxy]phenyl]propane (hereinafter sometimes referred to as "Bis3"), 2-[4-[3-(meth)acryloyloxy-2-hydroxypropoxy]phenyl]-2-[4-(meth)acryloyloxydiethoxy phenyl]propane, 2-[4-[3-(meth)acryloyloxy-2-hydroxypropoxy]phenyl]-2-[4-

(meth)acryloyloxytriethoxy phenyl]propane, 2-[4-[3-(meth)acryloyloxy-2-hydroxypropoxy]phenyl]-2-[4-(meth)acryloyloxy dipropoxyphenyl]propane, and the like. These polymerizable monomers can be used alone, or as a mixture of two or more thereof. Among these, Bis-GMA is preferable from the viewpoint of the mechanical strength as a cured product of the dental composition.

From the viewpoint of the mechanical strength as a cured product of the dental composition, the content of the polymerizable monomer (a) is preferably 10 to 80% by mass per 100% by mass of the polymerizable monomer component (A), and more preferably 30 to 50% by mass.

The aromatic polymerizable monomer (b) not having a hydroxyl group is a polymerizable monomer having at least one aromatic ring and at least one polymerizable group but not having a hydroxyl group. The numbers of aromatic rings and polymerizable groups are not particularly limited. From the viewpoints of the availability and the mechanical strength as a cured product of the dental composition, the number of polymerizable groups is preferably 1 to 6, and more preferably 2 to 4. From the viewpoints of the availability and the mechanical strength as a cured product of the dental composition, the number of aromatic rings is preferably 1 to 3, and more preferably 2. It is particularly preferable that the polymerizable monomer (b) has a bisphenol A skeleton. An example of such a polymerizable monomer (b) is a compound represented by the following formula (I):

From the viewpoints of the mechanical strength as a cured product of the dental composition and the handling properties, the content of the polymerizable monomer (b) is preferably 10 to 80% by mass per 100% by mass of the polymerizable monomer component (A), and more preferably 20 to 70% by mass.

The aliphatic polymerizable monomer (c) can be used without any particular limitation as long as it is a polymerizable monomer not having an aromatic ring. From the viewpoints of the availability and the mechanical strength as a cured product of the dental composition, the number of polymerizable groups is preferably 1 to 6. The aliphatic polymerizable monomer (c) may be either an aliphatic polymerizable monomer (c-1) not having a hydroxyl group or an aliphatic polymerizable monomer (c-2) having a hydroxyl group.

Examples of the polymerizable monomer (c-1) include methyl(meth)acrylate, ethyl(meth)acrylate, propyl(meth)acrylate, isopropyl(meth)acrylate, butyl(meth)acrylate, isobutyl(meth)acrylate, lauryl(meth)acrylate, 2,3-dibromopropyl (meth)acrylate, (meth)acrylamide, ethylene glycol di(meth)acrylate, triethylene glycol di(meth)acrylate (hereinafter sometimes referred to as "3G"), 1,2-butanediol di(meth)acrylate, neopentyl glycol di(meth)acylate, propylene glycol di(meth)acrylate, 1,3-butanediol di(meth)acrylate, 1,4-butanediol di(meth)acrylate, 1,6-hexanediol di(meth)acrylate, 1,10-decanediol di(meth)acrylate (hereinafter sometimes referred to as "DD"), 2,2,4-trimethylhexam-

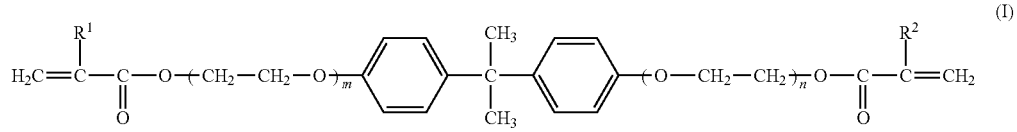

(I)

where $R^1$ and $R^2$ are independently a hydrogen atom or a methyl group, m and n are 0 or positive integers representing an average number of added moles of ethoxy groups, and the sum of m and n is preferably 1 to 6, and more preferably 2 to 4. Examples of such a compound include 2,2-bis[4-(meth)acryloyloxypolyethoxyphenyl]propane with m+n of 2.6 (hereinafter sometimes referred to as "D2.6E"), 2,2-bis[4-(meth)acryloyloxypolyethoxyphenyl]propane with m+n of 6 (2,2-bis[4-(meth)acryloyloxytriethoxyphenyl]propane (hereinafter sometimes referred to as "D6E"), 2,2-bis[4-(meth)acryloyloxyphenyl]propane (with m+n of 0), 2-[4-(meth)acryloyloxyethoxyphenyl]-2-[4-(meth)acryloyloxyphenyl]propane (with m+n of 1), 2,2-bis[4-(meth)acryloyloxyethoxyphenyl]propane (with m+n of 2), 2-[4-(meth)acryloyloxydiethoxyphenyl]-2-[4-(meth)acryloyloxyethoxyphenyl]propane (with m+n of 3), 2,2-bis[4-(meth)acryloyloxydiethoxyphenyl]propane (with m+n of 4), 2-[4-(meth)acryloyloxydiethoxyphenyl]-2-[4-(meth)acryloyloxytriethoxyphenyl]propane (with m+n of 5), and the like. As the polymerizable monomer (b), 2,2-bis[4-(meth)acryloyloxydipropoxyphenyl]propane, 2-[4-(meth)acryloyloxydipropoxyphenyl]-2-[4-(meth)acryloyloxytriethoxyphenyl]propane, 2,2-bis[4-(meth)acryloyloxypropoxyphenyl]propane, 2,2-bis[4-(meth)acryloyloxyisopropoxyphenyl]propane, or the like also can be used. These polymerizable monomers can be used alone, or as a mixture of two or more thereof. Among these, D2.6E and D6E are preferable from the viewpoint of the properties (such as a precipitation property) of the polymerizable monomers.

ethylene bis(2-carbamoyloxyethyl) di(meth)acrylate (hereinafter sometimes referred to as "UDMA"), N,N'-(2,2,4-trimethylhexamethylene)bis[2-(aminocarboxy)propane-1,3-diol]tetra (meth)acrylate, trimethylolpropane tri(meth)acrylate, trimethylolethane tri(meth)acrylate, pentaerythritol tetra(meth)acrylate, and 1,7-diacryloyloxy-2,2,6,6-tetraacryloyloxymethyl-4-oxyheptane.

Examples of the polymerizable monomer (c-2) include 2-hydroxyethyl (meth)acrylate, 2-hydroxypropyl(meth)acrylate, 3-hydroxypropyl(meth)acrylate, 1,3-dihydroxypropyl(meth)acrylate, 2,3-dihydroxypropyl(meth)acrylate, 2-hydroxyethyl(meth)acrylamide, 1,2-bis(3-methacryloyloxy-2-hydroxypropoxy)ethane, diethylene glycol (meth)acrylate, pentaerythritol di(meth)acrylate, and tetramethylolmethane tri(meth)acrylate. These polymerizable monomers can be used alone, or as a mixture of two or more thereof. In the present description, (meth)acrylates include acrylic acid esters and methacrylic acid esters.

From the viewpoint of handling properties, the content of the polymerizable monomer (c) is preferably 5 to 45% by mass per 100% by mass of the polymerizable monomer component (A), and more preferably 10 to 35% by mass.

In the present invention, the polymerizable monomer component (A) having the above-described structure and a novel filler (B) to be described later are used in combination. Therefore, not only the dental composition exhibits extremely high transparency, but also high paste handling properties can be achieved simultaneously. Furthermore, from the viewpoint of obtaining high transparency when the filler (B) is used in combination, the refractive index of the polymer obtained by polymerizing the polymerizable monomer component (A) is preferably 1.52 to 1.58. The refractive index of a polymer obtained by polymerizing a polymerizable monomer usually is slightly higher than that of the polymerizable monomer. Therefore, to control the refractive index of the above polymer in the range of 1.52 to 1.58, a combination of the polymerizable monomers (a) to (c) may be selected and their content ratio may be adjusted so that the refractive index of the resulting polymerizable monomer component (A) can have a value slightly lower than 1.52 to 1.58.

In the present invention, the amorphous powder (B) including silica-based fine particles and coatings of an oxide that cover the surfaces of the silica-based fine particles is used. The oxide contains a zirconium atom, a silicon atom, and an oxygen atom.

The silica-based fine particles mean fine particles containing 80 mol % or more of $SiO_2$ in terms of oxides. The components other than $SiO_2$ are not particularly limited as long as they do not impair the advantageous effects of the present invention. Examples of the components include $TiO_2$, $ZrO_2$, $Al_2O_3$, and $Na_2O$. Preferably, the content of $SiO_2$ is 90 mol % or more. It is preferable that the content of $SiO_2$ be substantially 100 mol % (that is, the content be 100% except for unavoidable impurities). Preferably, the average particle size of the silica-based fine particles is 2 to 300 nm. When the average particle size is less than 2 nm, the resulting cured product of the dental composition may have insufficient mechanical strength. When the dental composition containing the silica-based fine particles having an average particle size of more than 300 nm is used to restore teeth, the cured product may have insufficient surface smoothness and gloss after polishing. The average particle size of the silica-based fine particles can be determined by the dynamic light scattering method. For example, 7.0 g of an aqueous dispersion sol containing silica fine particles (having a solid content of 20% by weight) is placed in a cylindrical stainless steel cell of 3 cm long, 2 cm wide and 2 cm high equipped with a transmission window, and the particle size distribution is measured using an ultrafine particle size distribution analyzer of dynamic light scattering type (Model 9340-UPA150 manufactured by Honeywell). Thus, the average particle size can be calculated.

In the present invention, an "amorphous" filler (B) means that when the inorganic powder obtained as the filler (B) is subjected to an X-ray diffraction analysis by X-ray diffractometry using an X-ray diffractometer ("RINT-1400" manufactured by Rigaku Corporation) under the following conditions, no diffraction peak is observed.
(Conditions for X-Ray Diffraction Analysis)
2θ: 10-70 degrees
Scan speed: 2 degrees/min
Tube voltage: 30 kV
Tube current: 130 mA The oxide that covers the surface of the silica-based fine particle contains a zirconium atom, a silicon atom, and an oxygen atom. The oxide further may contain a titanium atom, an aluminum atom, etc. This oxide coating on the surface of the silica-based fine particle approximates the refractive index of the filler (B) to that of the polymerizable monomer component (A). As a result, the dental composition exhibits excellent transparency, and the cured product of the dental composition has high mechanical strength.

Specific examples of the structure of the oxide are shown below.

[Chemical Formula 2]

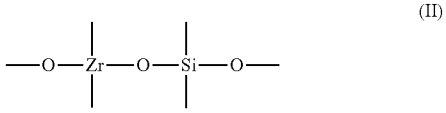

[Chemical Formula 3]

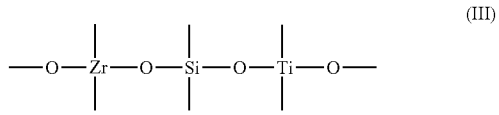

[Chemical Formula 4]

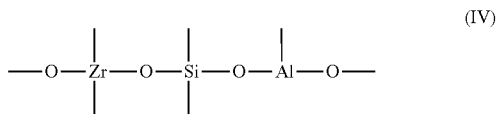

In the filler (B), the oxide coating may cover each of the silica-based fine particles, or may cover a plurality of silica-based fine particles. In the preferred embodiment, the oxide coating covers a plurality of silica-based fine particles. In this case, the filler (B) has a structure in which the oxide coating of a silica-based fine particle and the oxide coating of a neighboring silica-based fine particle are connected with each other. In this regard, it is preferable that the filler (B) have a structure in which the oxide coating of a silica-based fine particle and the oxide coating of a neighboring silica-based fine particle extend and are connected with each other. In the case where the silica-based fine particles are connected through the oxide coatings in the manner as described above, the silica-based fine particles are bonded to each other more strongly than they are aggregated together by intermolecular force. Accordingly, the use of this filler (B) in the dental material further increases the mechanical strength. Furthermore, as the dental material is abraded, the connecting portion between the oxide coatings is ruptured and thereby only a part of the filler (B) comes off. Therefore, the use of this filler (B) also increases the surface smoothness and gloss after polishing. From the viewpoint of the surface smoothness and gloss after polishing, it is preferable that, in the outer shape of this connection structure, the connecting portion between the oxide coatings be thinner than a portion where the silica-based fine particle is covered by the oxide coating. In other words, it is preferable that the thickness of the connecting portion between the oxide coatings be smaller than the sum of the largest dimension of the silica-based fine particle in the thickness direction and the thicknesses of two portions of the oxide coating of that particle.

Figure 2:
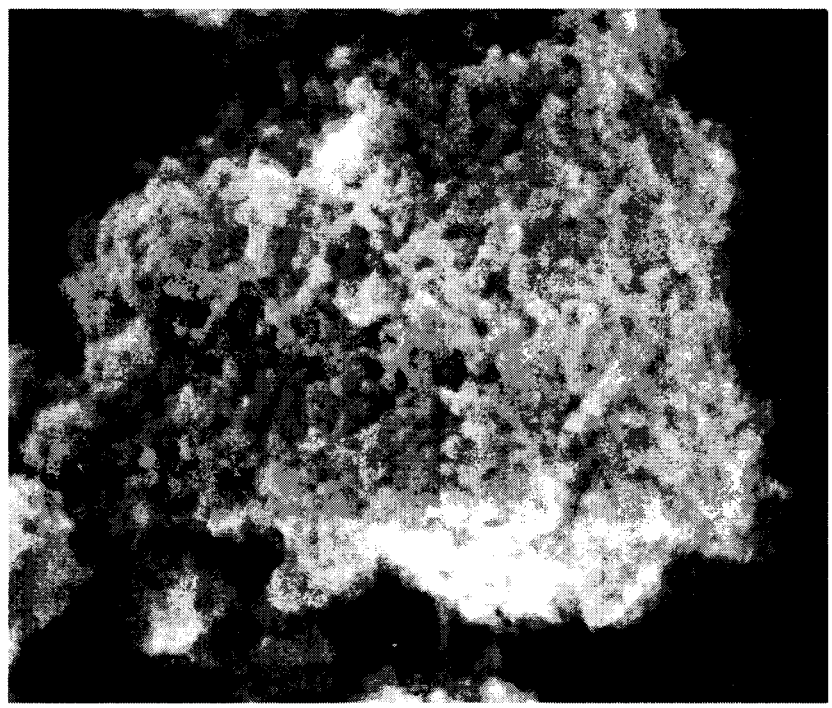
FIG. 2 is an SEM micrograph (×300000) of another example of an amorphous filler (B) which has been subjected to a drying process.

It is more preferable, in the structure of the filler (B), that one oxide coating of a silica-based fine particle is connected with a plurality of oxide coatings of neighboring silica-based fine particles. In this case, the filler (B) may have a structure, such as a tetrapod structure, or a star structure, in which a plurality of silica-based fine particles are connected through the oxide coatings to one silica-based fine particle with the one silica-based fine particle being placed in the center of the structure, or may have a branched three-dimensional network structure, in which the plurality of silica-based fine particles connected to one silica-based fine particle through the oxide coatings are connected further with other silica-based fine particles. In this three-dimensional network structure, silica-based fine particles are present at the ends of the branches and the branch points. Silica-based fine particles may be present at positions other than the ends of the branches and the branch points. It is particularly preferable that the filler (B) have a porous particle structure in which the oxide coatings are connected to each other to form an aggregate of the silica-based fine particles covered with the oxide coatings. FIG. 1 and FIG. 2 show SEM micrographs of examples of the filler (B) used in the present invention.

The thickness of the oxide coating may be determined appropriately in consideration of the particle size of the above silica-based fine particles, the thickness of the surface-treated layer to be described later, and the particle size of the filler (B) to be described later.

The filler (B) may further include, if necessary, a surface-treated layer of at least one organic metal compound selected from the group consisting of an organic silicon compound, an organic titanium compound, an organic zirconium compound, and an organic aluminum compound on the oxide coating. With this surface-treated layer, the refractive index of the filler (B) can be adjusted. Furthermore, this surface-treated layer enhances the dispersibility of the filler (B) in the polymerizable monomer component (A) and the adhesion between the polymerizable monomer component (A) and the filler (B). When two or more different kinds of organic metal compounds are used, the surface-treated layer may be made of a mixture of these two or more different kinds of organic metal compounds, or may have a multilayer structure in which the two or more different organic metal compound layers are laminated.

An example of the organic silicon compound is a compound represented by $R^3{}_n SiX_{4-n}$ (where $R^3$ is a substituted or unsubstituted hydrocarbon group having 1 to 13 carbon atoms, X is an alkoxy group having 1 to 4 carbon atoms, a hydroxyl group, a halogen atom, or a hydrogen atom, and n is an integer of 0 to 3. If a plurality of $R^3$s and a plurality of Xs are present, the $R^3$s may be the same as or different from one another, and the Xs may be the same as or different from one another.)

Specific examples of the organic silicon compound include methyltrimethoxysilane, dimethyldimethoxysilane, phenyltrimethoxysilane, diphenyldimetoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyl-tris(β-methoxyethoxy)silane, 3,3,3-trifluoropropyl trimethoxysilane, methyl-3,3,3-trifluoropropyl dimethoxysilane, β-(3,4-epoxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloxypropylmethyldimethoxysilane, γ-methacryloxypropylmethyldiethoxysilane, N-β(aminoethyl)γ-aminopropylmethyldimethoxysilane, N-β(aminoethyl)γ-aminopropyltrimethoxysilane, N-β(aminoethyl)γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloxyalkyl trimethoxysilane (having 3 to 13 carbon atoms between a (meth)acryloxy group and a silicon atom, for example, γ-methacryloxypropyltrimethoxysilane, or the like), ω-(meth)acryloxyalkyl triethoxysilane (having 3 to 13 carbon atoms between a (meth)acryloxy group and a silicon atom, for example, γ-methacryloxypropyltriethoxysilane, or the like), and the like.

Among them, a coupling agent having a functional group that is copolymerizable with the polymerizable monomer component (A), for example, ω-(meth)acryloxyalkyl trimethoxysilane (having 3 to 13 carbon atoms between a (meth)acryloxy group and a silicon atom), ω-(meth)acryloxyalkyl triethoxysilane (having 3 to 13 carbon atoms between a (meth)acryloxy group and a silicon atom), vinyltrimethoxysilane, vinyltriethoxysilane, vinyltriacetoxysilane, γ-glycidoxypropyltrimethoxysilane, or the like is used particularly preferably in the dental composition of the present invention.

More preferable examples of the organic silicon compound include 8-methacryloyloxyoctyltrimethoxysilane, 9-methacryloyloxynonyltrimethoxysilane, 10-methacryloyloxydecyltrimethoxysilane, 11-methacryloyloxyundecyltrimethoxysilane, 11-methacryloyloxyundecyldichloromethylsilane, 11-methacryloyloxyundecyltrichlorosilane, 11-methacryloyloxyundecyldimethoxymethylsilane, 12-methacryloyloxydodecyltrimethoxysilane, 13-methacryloyloxytridecyltrimethoxysilane, and the like. These organic silicon compounds can be used alone, or as a mixture of two or more thereof. Among these, from the viewpoint of achieving a good balance between an increase in the content of the filler and a low viscosity, 8-methacryloyloxyoctyltrimethoxysilane, 9-methacryloyloxynonyltrimethoxysilane, 10-methacryloyloxydecyltrimethoxysilane, and 11-methacryloyloxyundecyltrimethoxysilane are used preferably.

Examples of the organic titanium compound include tetramethyl titanate, tetraisopropyl titanate, tetra-n-butyl titanate, butyl titanate dimmer, tetra(2-ethylhexyl) titanate, and the like.

Examples of the organic zirconium compound include zirconium isopropoxide, zirconium-n-butoxide, zirconium acetylacetonate, zirconyl acetate, and the like.

Examples of the organic aluminum compound include aluminum acetylacetonate and a chelate compound of a salt of aluminum and an organic acid.

In the present invention, irregular-shaped, and/or spherical or nearly spherical particles can be used as the filler (B), but preferably, the filler (B) particles are spherical or nearly spherical to increase the content thereof. For example, the percentage of the spherical particles in the filler (B) is preferably at least 60%. More preferably, the filler (B) consists of the spherical particles (i.e., the percentage of the spherical particles in the filler (B) is 100%). The filler (B) particles having this shape can be obtained easily by spray-drying a mixed liquid containing silica-based fine particles whose surfaces are covered with coatings of an oxide containing at least a zirconium atom, a silicon atom, and an oxygen atom. The use of the filler (B) having such a shape increases the content of the filler itself while maintaining the low viscosity of the dental composition. As a result, the dental composition of the present invention having excellent surface smoothness and gloss after polishing and excellent paste handling properties while maintaining high strength can be obtained easily.

In the present description, the "spherical", "nearly spherical", and "irregular" shapes are those determined and classified according to the evaluation of the shapes of the particles of the filler (B) observed in a unit field of view of a micrograph taken with a scanning electron microscope (hereinafter abbreviated as "SEM"). Specifically, among the particles observed in the SEM micrograph, rounded particles with a proportion of at least 0.9 are classified as "spherical", particles with a proportion of at least 0.6 but less than 0.9 are classified as "nearly spherical", and particles other than the "spherical" and "nearly spherical" ones are classified as "irregular-shaped", when the proportion is obtained by dividing the diameter of a particle perpendicular to its maximum diameter by the maximum diameter. In the present description, the "spherical particles" include both the particles classified as "spherical" and "nearly spherical" according to the evaluation method.

Furthermore, in the present description, the percentage of the spherical particles in the filler (B) means the percentage of the total number of particles classified as spherical and nearly spherical in the 100 particles each observed in the SEM micrograph and evaluated by the method as described above.

The average particle size of the filler (B) is 1 to 20 μm, preferably 2 to 15 μm, and more preferably 3 to 10 μm. When the average particle size is less than 1 μm, the resulting cured product of the dental composition has insufficient mechanical strength. On the other hand, when the average particle size exceeds 20 μm, the sagging of the paste develops, which degrades the handling properties. Particularly, when the number of particles of 0.5 μm or less accounts for 10% or less and the number of particles of 30 μm of more accounts for 10% or less in the particle size distribution of the filler (B), the mechanical strength and handling properties are improved more significantly. Thus, such a filler (B) is preferable. If the filler (B) consists of aggregated particles, the above-mentioned average particle size is the average particle size of the aggregated particles.

The average particle size of the filler (B) can be obtained by the laser diffraction/scattering method. More specifically, for example, the average particle size can be obtained by the measurement using a 0.2% aqueous solution of sodium hexametaphosphate as a dispersion medium, with a laser diffraction particle size distribution analyzer (SALD-2100 manufactured by Shimadzu Corporation). As stated herein, the average particle size refers to the volume median particle size, which is a particle size at a cumulative volume frequency of 50% when calculated based on the volume fraction of the particles from the smaller particle size side.

It is preferable that the refractive index of the filler (B) be 1.52 to 1.58. When the refractive index of the filler (B) is within this range, it is easy to make the refractive index of the filler (B) equal to the refractive index of the polymerizable monomer component (A) if it also is 1.52 to 1.58. Thus, the transparency of the cured product of the dental composition can be increased easily. The refractive index of the filler (B) can be controlled by adjusting the content ratio of the metal elements in the oxide, forming the above-described surface-treated layer, etc.

The amount of the filler (B) to be added is 20 to 500 parts by weight per 100 parts by weight of the polymerizable monomer component (A), preferably 100 to 400 parts by weight, and more preferably 200 to 350 parts by weight. In the dental composition of the present invention, the filler (B) has a structure in which surfaces of silica-based fine particles are covered with coatings of an oxide containing a zirconium atom, a silicon atom, an oxygen atom, etc. Therefore, the content of the filler (B) can be increased while a significant increase in the viscosity is prevented. As a result, the dental composition can achieve high strength and high polishability, and further has excellent handling properties.

There is no particular limitation on the production method of the filler (B). For example, the filler (B) can be produced by the following steps:

(1) adding a hydroxide of an alkali metal and hydrogen peroxide to an aqueous solution containing a zirconium oxide hydrate and stirring the mixture to prepare a mixed aqueous solution in which the zirconium oxide hydrate is peptized;

(2) adding, under stirring, the mixed aqueous solution obtained in the above step (1) and an aqueous solution of a silicic acid solution to a silica sol in which silica-based fine particles having an average particle size of 2 to 300 nm are dispersed in water;

(3) treating the mixed aqueous solution obtained in the above step (2) with a cation-exchange resin to remove alkali cations;

(4) putting the mixed aqueous solution obtained in the above step (3) into a reaction vessel and subjecting the mixed aqueous solution to a hydrothermal treatment at a temperature of 100 to 350° C. to prepare a mixed aqueous solution containing the filler (B) in which the surfaces of the silica-based fine particles are covered with coatings of an oxide containing at least a zirconium atom, a silicon atom, and an oxygen atom; and (5) drying the filler (B) contained in the mixed aqueous solution obtained in the above step (4).

The zirconium oxide hydrate ($ZrO_2 \cdot xH_2O$) used in the step (1) can be prepared by a conventionally known method, for example, by hydrolyzing a zirconium salt in an aqueous solution, or by adding alkali or ammonia to an aqueous solution of a zirconium salt to cause a neutralization reaction. The zirconium oxide hydrate is obtained, for example, by adding, under stirring, ammonia or aqueous ammonia to an aqueous solution of one or more zirconates selected from zirconium oxychloride, zirconium oxysulfate, zirconium oxynitrate, zirconium oxyacetate, zirconium oxycarbonate, and ammonium zirconium oxycarbonate to obtain a neutralized reaction product, and washing the neutralized reaction product.

The hydroxide of an alkali metal ($M_2O$) used in the above step (1) is, for example, potassium hydroxide, sodium hydroxide, etc. Among them, potassium hydroxide is used preferably.

Preferably, this hydroxide of an alkali metal is added at a molar ratio to the zirconium oxide hydrate ($M_2O/ZrO_2 \cdot xH_2O$) of 1/1 to 10/1.

Preferably, the hydrogen peroxide ($H_2O_2$) used in the above step (1) is added at a molar ratio to the zirconium oxide hydrate ($H_2O_2/ZrO_2 \cdot xH_2O$) of 5/1 to 30/1.

As the silica sol used in the above step (2), any commercially available product (for example, SI-30 manufactured by Catalysts and Chemicals Industries Co., Ltd.) may be used as long as the product contains silica-based fine particles having an average particle size of 2 to 300 nm. The concentration of the silica-based fine particles contained in the silica sol is preferably in the range from 0.5 to 5% by weight.

The aqueous solution of the silicic acid solution (hereinafter sometimes referred to simply as a "silicic acid solution") used in the above step (2) is obtained, for example, by treating an aqueous solution of a silicate, for example, an alkali metal silicate such as sodium silicate (water glass) or potassium silicate, or an organic base silicate such as quaternary ammonium silicate, with a cation-exchange resin to remove alkali cations.

It is preferable to use, among these aqueous solutions of the silicic acid solution, an aqueous solution having a pH of 2 to 4 and a silicon content of 0.5 to 5% by weight in terms of $SiO_2$.

It is preferable that the mixed aqueous solution -(1) obtained in the above step (1) and the silicic acid solution be prepared respectively so that the molar ratio ($ZrO_2/SiO_2$-(1)) is 1/16 to 1/1, when the zirconium components in the mixed aqueous solution -(1) are expressed as $ZrO_2$ and the silicon components contained in the silicic acid solution are expressed as $SiO_2$-(1), and that they be added together slowly into the silica sol.

It is also preferable that the amount of these solutions to be added to the silica sol be in the range of 7/100 to 15/10 in terms of weight ratio {(ZrO$_2$/SiO$_2$-(1))/SiO$_2$-(2)}, when the silica-based fine particles are expressed as SiO$_2$-(2), although the amount to be added varies depending on the degree of coating of the silica-based fine particles contained in the silica sol. Preferably, the silica sol is heated previously to a temperature of 70 to 95° C. before these solutions are added.

When the mixed aqueous solution -(1) and the aqueous solution of the silicic acid solution are added under stirring to the silica sol, as described above, the zirconium components and the silicon components undergo hydrolysis reactions in the mixed aqueous solution -(2), and the surfaces of the silica-based fine particles contained in the silica sol are covered with coatings of partial hydrolysates or hydrolysates of the above components.

As the mixed aqueous solution -(1) having strong alkalinity is added to the silica sol, the pH of the mixed aqueous solution -(2) increases with time. Therefore, it is desirable to stop the addition of the mixed aqueous solution -(1) and the silicic acid solution when the pH of the mixed aqueous solution -(2) approaches 11. When the pH exceeds 11, the silica-based fine particles contained in the silica sol begin to be dissolved in the mixed aqueous solution -(2) due to the alkalinity, which is not preferable.

Therefore, if the addition of the mixed aqueous solution -(2) and the silicic acid solution has not yet been completed at the time when the pH reaches 11, it is preferable that the step (3) as described below be performed to remove alkali cations, and then the operation of the step (2) be carried out again or be repeated.

In the step (3), the mixed aqueous solution -(2) obtained in the step (2) is subjected to a treatment with a cation-exchange resin to remove alkali cations. There is no particular limitation on the cation-exchange resin used in this step. It is preferable to use a cation-exchange resin such as SK1BH manufactured by
Mitsubishi Chemical Corporation.

In this step, it is preferable that the mixed aqueous solution -(2) be subjected to the above treatment for removing alkali cations so that the mixed aqueous solution -(2) has a pH of 7.0 to 10.0.

In the above step (4), the mixed aqueous solution -(3) obtained in the step (3) is subjected to a hydrothermal treatment in a reaction vessel at a temperature of 100° C. to 350° C. The reaction vessel is not particularly limited as long as it is a pressure and heat resistant vessel capable of withstanding a pressure of 0.5 to 16.5 MPa, and a stainless steel autoclave is used preferably.

Thus, a mixed aqueous solution -(4) containing the filler (B) in which the surfaces of the silica-based fine particles are covered with coatings of an oxide containing at least a zirconium atom, a silicon atom, and an oxygen atom is obtained.

In the step (5), the solid product composed of the filler (B) contained in the mixed aqueous solution -(4) obtained in the step (4) is dried. The solid product contained in the mixed aqueous solution -(4) can be dried by being subjected to a commonly used conventional drying step, for example, a step of filtering the solid product from the mixed aqueous solution -(4), washing the filtered solid product with pure water or distilled water if necessary, and then drying the washed solid product by hot air at a temperature of 80 to 250° C.

It is desirable to subject the dried product obtained in this hot air drying step to a grinding step using a mortar and a ball mill, if necessary, to adjust the particle size. The resulting dried product has a partial structure, as shown in FIG. 1, for example, in which the oxide coating of a silica-based fine particle and the oxide coating of a neighboring silica-based fine particle extend and are connected to each other, and the oxide coatings each cover a plurality of silica-based fine particles. The resulting dried product has, as an overall structure, a porous particle structure, as shown in FIG. 2, for example, in which the oxide coatings are connected to each other to form an aggregate of the silica-based fine particles covered with the oxide coatings.

In the above step (5), the filler (B) of spherical particles in overall shape can be obtained by spray-drying the mixed aqueous solution -(4) with a spray dryer or the like. That is, the filler (B) can be obtained also by spray-drying a mixed liquid of a sol containing silica fine particles and a solution containing zirconium atoms and oxygen atoms. It is preferable that the mixed liquid to be spray-dried be prepared so that the content of silica-based fine particles is 5 to 50% by weight. If the content of silica-based fine particles in the mixed liquid is adjusted to the above range, particles having a desired particle size and particle size distribution can be prepared.

As described above, in the dental composition of the present invention, it is preferable that the filler (B) contain spherical particles, and that the percentage of the spherical particles be at least 60%. Therefore, it is preferable to prepare, by spray-drying, the filler (B) consisting of particles having a spherical overall shape. It is possible to use only the filler (B) consisting of spherical particles obtained by spray-drying. It is also possible to use in combination this filler (B) of spherical particles and the filler (B) obtained by adjusting the particle size of the dried product obtained in the above hot air drying step.

Thus, a dried amorphous powder or a ground product thereof consisting of inorganic oxide fine particles including silica-based fine particles covered with coatings of an oxide containing at least zirconium, silicon, and oxygen is obtained.

The dried amorphous powder or the ground product thereof obtained as above may be used as it is as the filler (B) used in the present invention, but it is preferable that the dried amorphous powder or the ground product thereof be calcined at a temperature of 300 to 900° C. in terms of the mechanical strength and wear resistance. A known method can be used for the calcining without any limitation. Preferably, the dried amorphous powder or the ground product thereof is calcined in a quartz crucible placed in an electric furnace.

The calcined product as the filler (B) (calcined amorphous powder) can be obtained easily by calcining the dried amorphous powder in the manner as described above. The shape of the particles of the calcined product is almost the same as that of the particles of the above-mentioned dried amorphous powder, although some of the particles are contracted.

Accordingly, the calcined product of the filler (B) also can have a porous particle structure in which the oxide coatings are connected to each other to form an aggregate of the silica-based fine particles covered with the oxide coatings. The calcined product obtained in the calcining step may be subjected to the grinding step using a mortar, a ball mill, etc., if necessary, to adjust the particle size.

In the dental composition of the present invention, the addition of the inorganic particles (C) further increases the strength, and the further addition of a small amount of inorganic ultrafine particles (D) further improves the forming property of the dental composition.

For the inorganic particles (C) used in the dental composition of the present invention, any known inorganic particles used for dental compositions can be used without any limitation. Examples of the inorganic particles include: various kinds of glass powders (containing silica as a main component and further containing an oxide of a heavy metal, boron, aluminum, and the like, if necessary: e.g., glass powders having typical compositions, such as fused silica, quartz, soda lime silica glass, E-glass, C-glass, borosilicate glass (Pyrex (registered trademark) glass); and glass powders for dental use, such as barium glass (GM 27884 and 8235 manufactured by Schott, and Ray-Sorb E-2000 and Ray-Sorb E-3000 manufactured by Specialty Glass), strontium borosilicate glass (Ray-Sorb E-4000 manufactured by Specialty Glass), lanthanum glass ceramics (GM 31684 manufactured by Schott), and fluoroaluminosilicate glass (GM 35429, G018-091, G018-117 manufactured by Schott); various kinds of ceramics; oxides such as silica-titania, and silica-zirconia; diatomaceous earth; kaolin; clay minerals (such as montmorillonite); activated white clay; synthetic zeolite; mica; calcium fluoride; ytterbium fluoride; yttrium fluoride; calcium phosphate; barium sulfate; zirconium dioxide; titanium dioxide; hydroxyapatite; and the like. Any one of the above-mentioned inorganic particles can be used alone or as a mixture of two or more kinds thereof. Among them, those containing silica as a main component are used preferably as the inorganic particles (C) in the dental composition of the present invention. The inorganic particles containing silica as a main component are the particles composed of an inorganic material containing at least 25% by weight of silica (preferably at least 40% by weight of silica).

The average particle size of the inorganic particles (C) is preferably 0.1 to 1.0 µm, more preferably 0.2 to 0.9 µm, and particularly preferably 0.4 to 0.7 µm. When the average particle size is less than 0.1 µm, the mechanical strength may be insufficient, or the paste becomes sticky, which may cause insufficient handling properties. When the average particle size exceeds 1.0 µm, the surface smoothness and gloss after polishing and the gloss durability as a cured product is impaired.

Like the filler (B), the inorganic particles (C) are used in combination with the polymerizable monomer component (A) for the dental composition. Therefore, it is desirable that the inorganic particles (C) be subjected previously to surface treatment with a surface treating agent to improve the affinity between the inorganic particles (C) and the polymerizable monomer component (A), and to increase the chemical bonding between the inorganic particles (C) and the polymerizable monomer component (A) so as to enhance the mechanical strength of the composite material. As such a surface treating agent, any one of the organic metal compounds described as examples for the filler (B) can be used likewise.

The average particle size of the inorganic particles (C) can be measured in the same manner as the average particle size of the filler (B) described above.

The shape of the inorganic particles (C) is not particularly limited. The inorganic particles (C) can be used as irregular-shaped or spherical (and nearly spherical) powder particles. If the irregular-shaped inorganic particles (C) are used, a dental composition having particularly excellent mechanical strength and wear resistance can be obtained, and if the spherical inorganic particles (C) are used, a dental composition having particularly excellent surface smoothness and gloss after polishing and gloss durability can be obtained. The shape of the inorganic particles (C) may be selected suitably in accordance with the intended use of the dental composition. The definition of the shape (spherical, nearly spherical, or irregular shape) of the inorganic particles (C) is the same as that of the filler (B).

The refractive index of the inorganic particles (C) is not particularly limited, but if it is approximated to the refractive indices of the polymerizable monomer component (A) and the filler (B), the transparency of the cured product of the dental composition can be enhanced easily. Therefore, the refractive index of the inorganic particles (C) is preferably 1.45 to 1.63, more preferably 1.50 to 1.60, and particularly preferably 1.52 to 1.58.

The amount of the inorganic particles (C) to be added is preferably 50 to 400 parts by weight per 100 parts by weight of the polymerizable monomer component (A), more preferably 150 to 350 parts by weight, and particularly preferably 150 to 300 parts by weight.

It is preferable that the dental composition of the present invention further contain the inorganic ultrafine particles (D). As the inorganic ultrafine particles (D), any known inorganic ultrafine particles used in dental compositions are used without any limitation. Preferable examples of the inorganic ultrafine particles (D) include particles of inorganic oxides such as silica, alumina, titania, zirconia, particles of composite oxides of any of these oxides, and particles of calcium phosphate, hydroxyapatite, yttrium fluoride, ytterbium fluoride, and the like. Preferably, the inorganic ultrafine particles (D) are particles of silica, alumina, titania, or the like prepared by flame pyrolysis, and examples thereof include products manufactured by Japan Aerosil Co., Ltd. under the trade names of Aerosil, Aeroxide Alu C, Aeroxide $TiO_2$ P 25, Aeroxide $TiO_2$ P 25S, VP Zirconium Oxide 3-YSZ, and VP Zirconium Oxide 3-YSZ PH.

The average particle size of the inorganic ultrafine particles (D) is preferably 5 to 50 nm, and more preferably 10 to 40 nm. The average particle size of the inorganic ultrafine particles (D) can be measured by the method described in Examples below. The shape of the inorganic ultrafine particles (D) is not particularly limited. The inorganic ultrafine particles (D) can be used as irregular-shaped or spherical (and nearly spherical) powder particles.

Like the filler (B) and the inorganic particles (C), the inorganic ultrafine particles (D) are used in combination with the polymerizable monomer component (A) for the dental composition. Therefore, it is desirable that the inorganic ultrafine particles (D) be subjected previously to surface treatment with a surface treating agent to improve the affinity between the inorganic ultrafine particles (D) and the polymerizable monomer component (A), and to increase the chemical bonding between the inorganic ultrafine particles (D) and the polymerizable monomer component (A) so as to enhance the mechanical strength of the composite material. As the surface treating agent, any one of the organic metal compounds described as examples for the filler (B) can be used likewise.

The amount of the inorganic ultrafine particles (D) to be added is preferably 10 to 50 parts by weight per 100 parts by weight of the polymerizable monomer, more preferably 10 to 40 parts by weight, and particularly preferably 10 to 20 parts by weight.

The dental composition of the present invention may contain inorganic particles (E) other than the filler (B), the inorganic particles (C), and the inorganic ultrafine particles (D) as long as the advantageous effects of the present invention are not impaired. For example, the inorganic particles (E) are particles of elements heavier than potassium. Examples of the elements include calcium, titanium, iron, zinc, strontium, zirconium, tin, barium, lanthanum, cerium, ytterbium, hafnium, tungsten, and the like. These elements can be used alone or in combination of two or more thereof.

The polymerizable monomer component (A) can be polymerized by a known method. It is preferable that the dental composition of the present invention further contain a polymerization initiator. The polymerization initiator can be selected from polymerization initiators commonly used in the industrial field. Among them, polymerization initiators used for dental applications are used preferably. Particularly, photopolymerization initiators and chemical polymerization initiators are used alone, or two or more of them are used in suitable combination.

Examples of the photopolymerization initiator include (bis)acylphosphine oxides, water-soluble acylphosphine oxides, thioxanthones or quaternary ammonium salts of thioxanthones, ketals, α-diketones, benzoin alkyl ether compounds, and α-amino ketone compounds.

Among (bis)acylphosphine oxides used as the photopolymerization initiator, examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis (2,4,6-trimethylbenzoyl)phenylphosphine oxide, and (2,5,6-trimethylbenzoyl)-2,4,4-trimethylpentylphosphine oxide.

Preferably, the water-soluble acylphosphine oxides used as the photopolymerization initiator have alkali metal ions, alkaline earth metal ions, pyridinium ions, or ammonium ions in the acylphosphine oxide molecules. For instance, the water-soluble acylphosphine oxides can be synthesized by the method disclosed in EP 0009348 B1 or JP 57 (1982)-197289A.

Specific examples of the aforementioned water-soluble acylphosphine oxides include sodium monomethylacetylphosphonate, sodium monomethyl(1-oxopropyl)phosphonate, sodium monomethylbenzoylphosphonate, sodium monomethyl(1-oxobutyl)phosphonate, sodium monomethyl(2-methyl-1-oxopropyl)phosphonate, sodium acetylphosphonate, sodium monomethylacetylphosphonate, sodium acetylmethylphosphonate, methyl-4-(hydroxymethoxyphosphinyl)-4-oxobutanoate sodium salt, methyl-4-oxophosphonobutanoate monosodium salt, acetylphenylphosphinate sodium salt, sodium (1-oxopropyl) pentylphosphinate, methyl-4-(hydroxypentylphosphinyl)-4-oxobutanoate sodium salt, sodium acetylpentylphosphinate, sodium acetylethylphosphinate, sodium methyl(1,1-dimethyl)methylphosphinate, sodium (1,1-diethoxyethyl)methylphosphinate, sodium (1,1-diethoxyethyl)methylphosphinate, methyl-4-(hydroxymethylphosphinyl)-4-oxobutanoate lithium salt, 4-(hydroxymethylphosphinyl)-4-oxobutanoic acid dilithium salt, methyl(2-methyl-1,3-dioxolan-2-yl) phosphinate sodium salt, methyl(2-methyl-1,3-thiazolidin-2-yl)phosphonite sodium salt, (2-methylperhydro-1,3-diazin-2-yl)phosphonite sodium salt, acetylphosphinate sodium salt, (1,1-diethoxyethyl)phosphonite sodium salt, (1,1-diethoxyethyl)methylphosphonite sodium salt, methyl(2-methyloxathiolane-2-yl)phosphinate sodium salt, methyl(2,4,5-trimethyl-1,3-dioxolan-2-yl)phosphinate sodium salt, methyl(1,1-propoxyethyl)phosphinate sodium salt, (1-methoxyvinyl) methylphosphinate sodium salt, (1-ethylthiovinyl) methylphosphinate sodium salt, methyl(2-methylperhydro-1,3-diazin-2-yl)phosphinate sodium salt, methyl(2-methylperhydro-1,3-thiazin-2-yl)phosphinate sodium salt, methyl(2-methyl-1,3-diazolidin-2-yl)phosphinate sodium salt, methyl(2-methyl-1,3-thiazolidin-2-yl)phosphinate sodium salt, (2,2-dicyano-1-methylethynyl)phosphinate sodium salt, acetylmethylphosphinate oxime sodium salt, acetylmethylphosphinate-O-benzyloxime sodium salt, 1-[(N-ethoxyimino)ethyl]methylphosphinate sodium salt, methyl(1-phenyliminoethyl)phosphinate sodium salt, methyl (1-phenylhydrazone ethyl)phosphinate sodium salt, [1-(2,4-dinitrophenylhydrazono)ethyl]methylphosphinate sodium salt, acetylmethylphosphinate semicarbazone sodium salt, (1-cyano-1-hydroxyethyl)methylphosphinate sodium salt, (dimethoxymethyl)methyl phosphinate sodium salt, formylmethylphosphinate sodium salt, (1,1-dimethoxypropyl)methylphosphinate sodium salt, methyl(1-oxopropyl)phosphinate sodium salt, dodecylguanidine salt of (1,1-dimethoxypropyl)methylphosphinate, isopropylamine salt of (1,1-dimethoxypropyl)methylphosphinate, acetylmethylphosphinate thiosemicarbazone sodium salt, 1,3,5-tributyl-4-methylamino-1,2,4-triazolium (1,1-dimethoxyethyl)-methylphosphinate, 1-butyl-4-butylaminomethylamino-3,5-dipropyl-1,2,4-triazolium (1,1-dimethoxyethyl)-methylphosphinate, 2,4,6-trimethylbenzoylphenylphosphine oxide sodium salt, 2,4,6-trimethylbenzoylphenylphosphine oxide potassium salt, and ammonium salt of 2,4,6-trimethylbenzoylphenylphosphine oxide. Furthermore, examples thereof also include compounds described in JP 2000-159621 A.

Among these (bis)acylphosphine oxides and water-soluble acylphosphine oxides, particularly preferable ones are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoylphenylphosphine oxide sodium salt.

Examples of thioxanthones or the quaternary ammonium salts of thioxanthones that are used as the above-mentioned photopolymerization initiators include thioxanthone, 2-chlorothioxanthen-9-one, 2-hydroxy-3-(9-oxy-9H-thioxanthen-4-yloxy)-N,N,N-trimethyl-propaneaminium chloride, 2-hydroxy-3-(1-methyl-9-oxy-9H-thioxanthen-4-yloxy)-N,N,N-trimethyl-propaneaminium chloride, 2-hydroxy-3-(9-oxo-9H-thioxanthen-2-yloxy)-N,N,N-trimethyl-propaneaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminium chloride, and 2-hydroxy-3-(1,3,4-trimethyl-9-oxo-9H-thioxanthen-2-yloxy)-N,N,N-trimethyl-1-propaneaminium chloride.

Among the thioxanthones or the quaternary ammonium salts of thioxanthones, a particularly preferable thioxanthone is 2-chlorothioxanthen-9-one, and a particularly preferable quaternary ammonium salt of thioxanthone is 2-hydroxy-3-(3,4-dimethyl-9H-thioxanthen-2-yloxy)-N,N,N-trimethyl-1-propaneaminium chloride.

Examples of ketals used as the photopolymerization initiator include benzyl dimethyl ketal and benzyl diethyl ketal.

Examples of the α-diketones used as the photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is particularly preferable from the viewpoint of having the maximum absorption wavelength in the visible light range.

Examples of the benzoin alkyl ethers used as the aforementioned photopolymerization initiator include benzoin methyl ether, benzoin ethyl ether, benzoin isopropyl ether, and benzoin isobutyl ether.

Examples of the α-aminoketones used as the aforementioned photopolymerization initiator include 2-methyl-1-[4-(methylthio)phenyl]-2-morpholinopropan-1-one.

Preferably, among these photopolymerization initiators, at least one selected from the group consisting of (bis)acylphosphine oxides, salts thereof, and α-diketones is used. This makes it possible to obtain a composition that has excellent photocurability in visible and near-ultraviolet ranges and sufficiently high photocurability regardless of which light source among a halogen lamp, light-emitting diode (LED), and xenon lamp is used.

Among the polymerization initiators used in the present invention, a chemical polymerization initiator that is used preferably is organic peroxide. The organic peroxide used as the chemical polymerization initiator is not particularly limited and a known one can be used. Examples of typical organic peroxides include ketone peroxide, hydroperoxide, diacyl peroxide, dialkyl peroxide, peroxyketal, peroxyester, and peroxydicarbonate.

Examples of the ketone peroxide used as the chemical polymerization initiator include methyl ethyl ketone peroxide, methyl isobutyl ketone peroxide, methylcyclohexanone peroxide, and cyclohexanone peroxide.

Examples of the hydroperoxide used as the chemical polymerization initiator include 2,5-dimethylhexane-2,5-dihydroperoxide, diisopropylbenzene hydroperoxide, cumene hydroperoxide, and t-butyl hydroperoxide.

Examples of the diacyl peroxide used as the chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxide used as the chemical polymerization initiator include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxyketal used as the chemical polymerization initiator include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and 4,4-bis(t-butylperoxy)valeric acid-n-butyl ester.

Examples of the peroxyester used as the chemical polymerization initiator include α-cumyl peroxyneodecanoate, t-butyl peroxyneodecanoate, t-butyl peroxypivarate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethyl hexanoate, t-butylperoxy acetate, t-butylperoxy benzoate, and t-butylperoxymaleic acid.

Examples of the peroxydicarbonate used as the chemical polymerization initiator include di-3-methoxy peroxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, diacyl peroxides are used preferably from the viewpoint of a comprehensive balance of safety, storage stability, and radical production ability, and among these, benzoyl peroxide is used particularly preferably.

The amount of the polymerization initiator to be added in the present invention is not particularly limited. However, from the viewpoint of, for example, curability of the resultant composition, it is preferable that 0.01 to 10 parts by weight of the polymerization initiator be contained per 100 parts by weight of the polymerizable monomer component (A), and it is more preferable that 0.1 to 5 parts by weight of the polymerization initiator be contained. When the amount of the polymerization initiator is less than 0.01 part by weight, polymerization may not proceed sufficiently and thereby mechanical strength may be reduced. Therefore, the amount is more preferably at least 0.1 part by weight. On the other hand, when the amount of the polymerization initiator exceeds 10 parts by weight, in the case where the polymerization initiator itself has low polymerization performance, sufficient mechanical strength may not be obtained and furthermore precipitation from the composition may occur. Therefore, the amount is more preferably 5 parts by weight or less.

In a preferred embodiment, a polymerization accelerator is used. Examples of the polymerization accelerator used in the present invention include amines, sulfinic acids and salts thereof, aldehydes, and thiol compounds.

Amines used as the polymerization accelerator can be divided into aliphatic amines and aromatic amines. Examples of aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, tertiary aliphatic amines are preferable from the viewpoint of curability and storage stability of the composition, and particularly, N-methyldiethanolamine and triethanolamine are used more preferably.

Examples of aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, 4-N,N-dimethylaminobenzoic acid ethyl ester, 4-N,N-dimethylaminobenzoic acid methyl ester, N,N-dimethylaminobenzoic acid n-butoxyethyl ester, 4-N,N-dimethylaminobenzoic acid 2-(methacryloyloxy)ethyl ester, 4-N,N-dimethylaminobenzophenone, and butyl 4-dimethylaminobenzoate. Among these, at least one selected from the group consisting of N,N-di(2-hydroxyethyl)-p-toluidine, 4-N,N-dimethylaminobenzoic acid ethyl ester, N,N-dimethylaminobenzoic acid n-butoxyethyl ester, and 4-N,N-dimethylaminobenzophenone is used preferably from the viewpoint of being capable of providing the composition with excellent curability.

Examples of the sulfinic acid or salt thereof used as the polymerization accelerator include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6- trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Sodium benzenesulfinate, sodium p-toluenesulfinate, and sodium 2,4,6-triisopropylbenzenesulfinate are particularly preferable.

Examples of aldehydes used as the polymerization accelerator include derivatives of terephthalaldehyde and benzaldehyde. Examples of the benzaldehyde derivative include dimethylaminobenzaldehyde, p-methyloxybenzaldehyde, p-ethyloxybenzaldehyde, and p-n-octyloxybenzaldehyde. Among these, from the viewpoint of curability, p-n-octyloxybenzaldehyde is used preferably.

Examples of the thiol compound used as the polymerization accelerator include 3-mercaptopropyltrimethoxysilane, 2-mercaptobenzoxazole, decanethiol, and thiobenzoic acid.

The amount of polymerization accelerator to be added in the present invention is not particularly limited. However, from the viewpoints of, for example, curability of the resultant composition, it is preferable that 0.001 to 10 parts by weight of polymerization accelerator be contained per 100 parts by weight of the polymerizable monomer component (A), and it is more preferable that 0.001 to 5 parts by weight of the polymerization accelerator be contained. When the amount of the polymerization accelerator is less than 0.001 part by weight, polymerization may not proceed sufficiently and mechanical strength may be reduced. Therefore, the amount is more preferably at least 0.05 part by weight. On the other hand, when the amount of the polymerization accelerator exceeds 10 parts by weight, in the case where the polymerization initiator itself has low polymerization performance, sufficiently high mechanical strength may not be obtained. Therefore, the amount is more preferably 5 parts by weight or less.

To the curable dental composition of the present invention, a pH adjuster, an ultraviolet absorber, an antioxidant, a polymerization inhibitor, a colorant, an antibacterial agent, an X-ray contrast agent, a thickening agent, a fluorescent agent, or the like can further be added in accordance with the intended use. Examples of the polymerization inhibitor include 2,6-di-butylhydroxytoluene, hydroquinone, dibutylhydroquinone, dibutylhydroquinone monomethyl ether, and 2,6-t-butylphenol. One or Two or more of these may be added.

The dental composition of the present invention contains at least the polymerizable monomer component (A) and the filler (B) having an average particle size in a specific range and a special structure as described above, and may further contain the inorganic particles (C) and the inorganic ultrafine particles (D) in accordance with the intended use. The dental composition of the present invention can be produced easily in a form suitable for the intended use (a one-paste form, a two-paste form, a powder-liquid form, or a molded form) by a method known to those skilled in the art. When a polymerization initiating function having chemical polymerizability or both chemical polymerizability and photopolymerizability is used, separate packages of a composition containing an organic peroxide (polymerization initiator) and a composition containing a reducing agent (polymerization accelerator) must be prepared so that the organic peroxide and the reducing agent are mixed together immediately before the use.

The viscosity of the dental composition of the present invention is in the range of 10 to 800 Pa·s, preferably in the range of 40 to 600 Pa·s, and more preferably 60 to 400 Pa·s. The dental composition having such a viscosity can achieve excellent handling properties particularly when it is used as a direct-filling treatment material. In the present description, the viscosity of the dental composition is measured by the method described in Examples below.

The dental composition of the present invention can be used suitably in a conventional manner as dental materials, for example, dental composite resins such as dental composite filling materials, dental crown materials, and luting materials, dental adhesives such as orthodontic adhesives, cavity coating adhesives, and dental fissure sealing materials, denture base materials, tissue conditioning materials for denture bases, fissure sealants, coating materials applied to tooth surfaces and dental prostheses, surface glazing materials, and dental lacquers. The cured product obtained by polymerizing and curing the dental composition of the present invention also can be molded to be used as artificial teeth, dentures, and resin blocks for CAD/CAM. Among them, the dental composition of the present invention can be used advantageously as a dental composite resin. This composite resin exhibits excellent surface smoothness and gloss after polishing and gloss durability as a cured product as well as good handling properties as a paste.

EXAMPLES

The present invention will be described in more detail below by the following examples, without intending to limit the scope of the present invention to these examples. The test methods, materials, etc. used in the examples are shown below. The test results of Examples 1 to 48 and Comparative Examples 1 to 5 to be described later are shown collectively in Table 1 to 5.

[Average Particle Sizes of Filler (B) and Inorganic Particles (C)]

The average particle sizes of the filler (B) and the inorganic particles (C) each are the volume median particle size thereof. The volume median particle size means a particle size at a cumulative volume frequency of 50% when calculated based on the volume fraction of the particles from the smaller particle size side. A laser diffraction particle size distribution analyzer (SALD-2100 manufactured by Shimadzu Corporation) was used to measure the particle size of each of the produced powders (the filler (B) and the inorganic particles (C)). As a dispersion medium, a 0.2% aqueous solution of sodium hexametaphosphate was used.

[Average Particle Size of Inorganic Ultrafine Particles (D)]

The inorganic ultrafine particles (D) were observed with a high performance scanning electron microscope (S-4500, manufactured by Hitachi Ltd.) under the condition of an acceleration voltage of 15 kV, and a 10000-magnification image thereof was obtained. The volumetric distribution of arbitrarily selected 100 particles was analyzed with an image-based particle size distribution analysis software (Mac-View ver. 3.5, manufactured by Mountech Co., Ltd.) to obtain the volume median particle size thereof.

[Viscosity]

The prepared paste (dental composition paste) was mounted on a rheometer (AR-2000, manufactured by TA Instruments, Japan), and the viscosity of the paste was measured at 25° C. Parallel plates with a diameter of 25 mm were rotated in one direction at a shear rate of 1.0 sec$^{-1}$ to measure the viscosity.

[Evaluation of Forming Property]

The prepared paste (dental composition paste) was extruded from a needle with a needle tip with a diameter of 0.80 mm onto a flat plate, and the shape of the paste was observed visually. Then, the forming property thereof was evaluated according to the following evaluation criteria. The pastes rated 2 to 5 were regarded as acceptable products.

(Evaluation Criteria of Forming Property)

1: A hemispherical shape is not formed, and the extruded shape remains unchanged.

2: A nearly hemispherical shape is formed, but the extruded shape is partially maintained.

3: A hemispherical shape is formed, and that shape is maintained.

4: A hemispherical shape is formed, but the height of the hemisphere decreases slightly.

5: A hemispherical shape is formed, but the height of the hemisphere decreases.

6: A hemispherical shape is not formed, or even if a hemispherical shape is formed, that shape is lost soon.

[Measurement of Consistency]

The prepared paste (dental composition paste) was allowed to stand still for five days in an incubator at a temperature of 60° C. (and a humidity of 40%). Then, the resulting paste was further allowed to stand still at 25° C. for 2 hours, and a test was performed to measure the consistency of the paste. 0.5 mL of the paste was placed in the shape of a mound in the center of a glass plate (5 cm×5 cm) in an incubator at a temperature of 25° C. (and a humidity of 40%). A glass plate (5 cm×5 cm) weighing 40 g was placed on the mound of paste. After 120 seconds, the longest and shortest diameters of the paste were measured through the glass plate, and the arithmetic mean of these diameters was calculated to obtain the consistency. The pastes having consistencies of 22 to 40 are regarded as acceptable products.

[Flexural Strength]

The prepared paste (dental composition paste) was filled in a stainless steel mold (with dimensions of 2 mm×2 mm×25 mm). The mold was clamped between upper and lower glass slides and the upper and lower surfaces of the mold were each exposed to light irradiation for 2 minutes with a light irradiator for dental laboratories (α-light II, manufactured by Morita). Thus, the paste was cured. Five cured products were prepared as test samples for each of the examples and comparative examples. Each of the cured products was taken out of the mold, and then stored in distilled water at 37° C. for 24 hours. The flexural strength of the cured product was measured using an Instron universal testing machine under the conditions of the span of 20 mm and the crosshead speed of 1 mm/min. The average value of the measured values of the five test samples was calculated to obtain the flexural strength. The cured products having flexural strengths of at least 130 MPa are regarded as acceptable products.

[Surface Smoothness and Gloss]

The produced dental composition was filled in a Teflon (registered trademark) mold (with dimensions of 10 mm×30 mm×1 mm). The mold was clamped between upper and lower glass slides, and the upper and lower surfaces of the mold were each exposed to light irradiation for 2 minutes. Thus, the composition was cured. The cured product was taken out of the mold, and then one surface of the cured product was polished with a #800 waterproof abrasive paper. Then, this polished surface was polished with Silicone Point M3 type HP13 manufactured by Shofu Inc. for 30 seconds under pouring water. The polished products having particularly excellent smoothness and gloss were rated A, those having excellent smoothness and gloss were rated B, and those having poor smoothness and gloss were rated C.

Preparation Example 1

Preparation of Precursor of Filler (B)

250 kg of zirconium oxychloride ($ZrOCl_2 \cdot 8H_2O$, manufactured by Taiyo Koko Co., Ltd.) was added to 4375 kg of pure water at a temperature of 15° C. and they were stirred to dissolve zirconium oxychloride therein.

250 L of aqueous ammonia with a concentration of 15% by weight was added slowly, under stirring, to the aqueous solution of zirconium oxychloride to cause a neutralization reaction of the zirconium oxychloride under the temperature condition of 15° C. Thus, a slurry containing the precipitate of zirconium oxide hydrate was obtained. The pH of this slurry was 8.5.

Next, this slurry was filtered, and the resulting cake-like material was washed repeatedly with pure water to remove by-products of the neutralization reaction and unreacted substances. As a result, 860 kg of a cake-like material consisting of 10% by weight of zirconium oxide hydrate in terms of $ZrO_2$ and water was obtained.

Next, 45800 g of pure water was added to 5416 g of the cake-like material containing zirconium oxide hydrate, and further 1024 g of potassium hydroxide with a purity of 85% (manufactured by Kanto Chemical Co., Inc.) was added under stirring to the above mixture to make the mixture alkaline. Then, 10248 g of hydrogen peroxide solution containing 35% by weight of hydrogen peroxide (manufactured by Hayashi Pure Chemical Industries, Ltd.) was added to the mixture.

Furthermore, this mixed aqueous solution was allowed to stand, under stirring, for one hour to peptize the zirconium oxide hydrate in the aqueous solution. Then, 39991 g of ice water obtained by freezing pure water was added to the resulting aqueous solution to cool the temperature of the aqueous solution, which had been raised by the exothermic reaction, to 30° C. or lower. As a result, 102400 g of a mixed aqueous solution (hereinafter referred to as a "prepared solution 1A") with a pH of about 11 and containing 0.5% by weight of zirconium components in terms of $ZrO_2$ was obtained.

10 Kg of commercially available water glass (manufactured by AGC Si-Tec. Co., Ltd.) was diluted with 38 kg of pure water, and then was treated with a cation-exchange resin (manufactured by Mitsubishi Chemical Corporation) to remove alkali cations contained therein. Thus, 9 kg of a silicic acid solution with a pH of 3 and containing 4% by weight of $SiO_2$ was prepared. Then, 10768 g of the silicic acid solution and 14860 g of pure water were mixed with each other to prepare 25628 g of a silicic acid solution containing 2% by weight of $SiO_2$.

Next, 47900 g of pure water was added to 3336 g of a silica sol containing 30% by weight of silica-based fine particles having an average particle size of 12 nm (SI-30, manufactured by Catalysts and Chemicals Industries Co., Ltd.), and the resulting mixture was stirred sufficiently. Thus, 51236 g of a silica sol containing 2% by weight of silica-based fine particles was obtained.

Next, the silica sol was heated to 90° C., and then 51200 g of the prepared solution 1A and 12814 g of the aqueous solution of the silicic acid solution were added slowly under stirring to the silica sol over 10 hours. As a result, 115250 g of a mixed aqueous solution with a pH of about 11 (hereinafter referred to as a "prepared solution 1B-(1)) was obtained.

Next, the prepared solution 1B-(1) was treated with a cation-exchange resin (SK1BH, manufactured by Mitsubishi Chemical Corporation) to remove alkali cations contained therein. As a result, 117250 g of a mixed aqueous solution with a pH of about 9.5 (hereinafter referred to as a "prepared solution 1C-(1)) was obtained.

Furthermore, 51200 g of the prepared solution 1A and 12814 g of the aqueous solution of the silicic acid solution were added slowly to the prepared solution 1C-(1) over 10 hours in the same manner as described above. As a result, 181264 g of a mixed aqueous solution with a pH of about 11 (hereinafter referred to as a "prepared solution 1B-(2)) was obtained.

Next, the prepared solution 1B-(2) was treated with a cation-exchange resin (SK1BH, manufactured by Mitsubishi Chemical Corporation) to remove alkali cations contained therein. As a result, 182264 g of a mixed aqueous solution with a pH of about 9.5 (hereinafter referred to as a "prepared solution 1C-(2)) was obtained.

Next, 100200 g of the prepared solution 1C-(2) was put in a stainless steel autoclave (manufactured by Taiatsu Techno Corporation), and was subjected to a hydrothermal treatment for 18 hours at a temperature of 165° C. As a result, 99750 g of a mixed aqueous solution (hereinafter referred to as a "prepared solution 1D) was obtained. This aqueous solution contained a filler in which the surfaces of silica-based fine particles were covered with coatings of an oxide containing a zirconium atom, a silicon atom, and an oxygen atom.

Preparation Example 2

Preparation of Spherical Dried Amorphous Powder 1A (with Average Particle Size of 10 µm)

The prepared solution 1D was pre-dried by spray drying in a micromist dryer "MDL-050" (manufactured by Fujisaki Electric Co., Ltd.) under the conditions of an inlet temperature of 200° C., an internal temperature of 70° C., an air flow rate of 30 mL/min, and a liquid flow rate of 23 mL/min. The powder thus obtained was dried by hot air at 200° C. for one hour. Thus, a spherical dried amorphous powder having an average particle size of 10 µm (hereinafter referred to as a dried powder 1A) was obtained. The dried powder 1A was observed in a SEM micrograph, and as a result, it was found that the dried powder 1A consists of spherical particles (100% spherical powder).

Preparation Example 3

Preparation of Spherical Dried Amorphous Powder 2A (with Average Particle Size of 3.0 µm)

Figure 3:
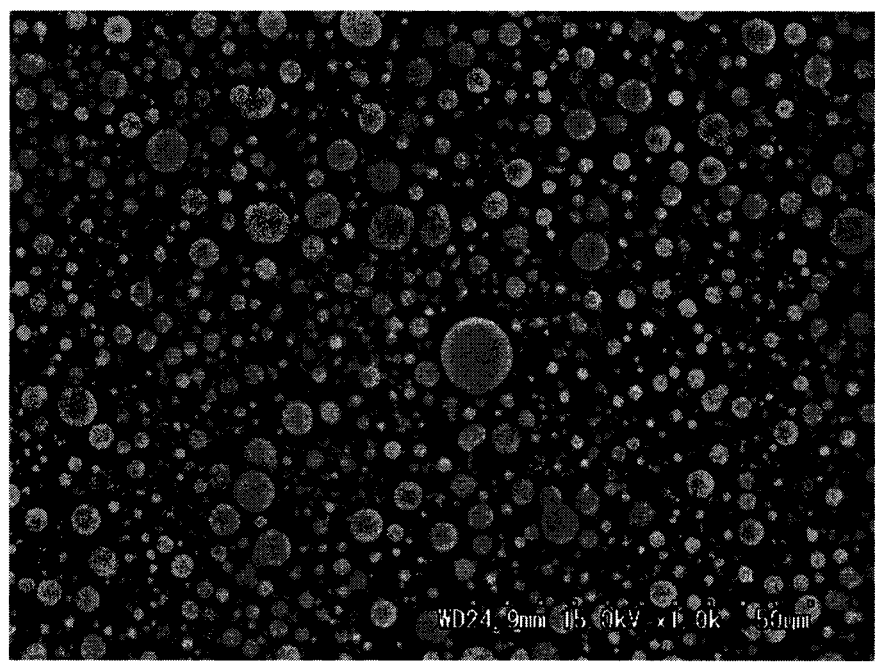
FIG. 3 is an SEM micrograph (×1000) of an amorphous filler (B) (dried powder 2A) which has been subjected to a drying process by a micromist dryer.

A spherical dried amorphous powder having an average particle size of 3.0 µm (hereinafter referred to as a dried powder 2A) was obtained in the same manner as in Preparation Example 2 except that the prepared solution 1D was dried under the conditions of an inlet temperature of 200° C., an internal temperature of 70° C., an air flow rate of 57 mL/min, and a liquid flow rate of 15 mL/min. The dried powder 2A was observed in a SEM micrograph, and as a result, it was found that the dried powder 2A consists of spherical particles (100% spherical powder) (see FIG. 3).

Preparation Example 4

Preparation of Spherical Dried Amorphous Powder 3A (with Average Particle Size of 20 µm)

The prepared solution 1D was pre-dried by spray drying in a spray dryer "ADL310" (manufactured by Yamato Scientific Co., Ltd.) under the conditions of an inlet temperature of 200° C., an internal temperature of 70° C., an air flow rate of 0.4 $m^3$/min, and a liquid flow rate of 15 mL/min. The powder thus obtained was dried by hot air at 200° C. for one hour. Thus, a spherical dried amorphous powder having an average particle size of 20 µm (hereinafter referred to as a dried powder 3A) was obtained. The dried powder 3A was observed in a SEM micrograph, and as a result, it was found that the dried powder 3A consists of spherical particles (100% spherical powder).

Preparation Example 5

Preparation of Dried Amorphous Powder 4A (with Average Particle Size of 10 µm)

The prepared solution 1D was dried in a hot air dryer at 90° C. to obtain a dried solid material, and this dried solid material was ground in a vibratory ball mill for 1.5 hours. Thus, an irregular-shaped dried amorphous powder having an average particle size of 10 µm (hereinafter referred to as a dried powder 4A) was obtained.

Preparation Example 6

Preparation of Spherical Dried Amorphous Powder 5A (with Average Particle Size of 25 µm)

The prepared solution 1D was dried in a spray dryer "ADL310" (manufactured by Yamato Scientific Co., Ltd.) under the conditions of an inlet temperature of 200° C., an internal temperature of 70° C., an air flow rate of 0.2 $m^3$/min, and a liquid flow rate of 15 mL/min. The powder thus obtained was dried by hot air at 200° C. for one hour. Thus, a spherical dried amorphous powder having an average particle size of 25 µm (hereinafter referred to as a dried powder 5A) was obtained. The dried powder 5A was observed in a SEM micrograph, and as a result, it was found that the dried powder 5A consists of spherical particles (100% spherical powder.

Preparation Example 7

Preparation of Spherical Dried Amorphous Powder 6A (with Average Particle Size of 0.7 µm)

The dried powder 2A was classified with a classifier (Elbow-Jet classifier manufactured by Matsubo Corporation). Thus, a spherical dried amorphous powder having an average particle size of 0.7 µm (hereinafter referred to as a dried powder 6A) was obtained.

Preparation Example 8

Preparation of Filler B-1 (with Average Particle Size of 10 µm)

The dried powder 1A was subjected to heat treatment in an electric furnace at 800° C. for one hour to obtain a spherical calcined amorphous powder having an average particle size of 10 µm. 100 g of the spherical calcined amorphous powder, 250 mL of toluene, and 30 g of 11-methacryloyloxyundecyltrimethoxysilane were charged into a three-necked flask equipped with a reflux tube, and the mixture was heated and refluxed under stirring. Toluene was distilled off under reduced pressure, and then the residue was vacuum-dried at 40° C. for 16 hours, and further heated at 90° C. for 3 hours. Thus, a filler B-1 having an average particle size of 10 μm, in which surface-treated layers are formed, was obtained.

Preparation Example 9

Preparation of Filler B-2 (with Average Particle Size of 3.0 μm)

The dried powder 2A was subjected to heat treatment in an electric furnace at 800° C. for one hour to obtain a spherical calcined amorphous powder having an average particle size of 3.0 μm. 100 g of the spherical calcined amorphous powder, 250 mL of toluene, and 30 g of 11-methacryloyloxyundecyl-trimethoxysilane were charged into a three-necked flask equipped with a reflux tube, and the mixture was heated and refluxed under stirring. Toluene was distilled off under reduced pressure, and then the residue was vacuum-dried at 40° C. for 16 hours, and further heated at 90° C. for 3 hours. Thus, a filler B-2 having an average particle size of 3.0 μm, in which surface-treated layers are formed, was obtained.

Preparation Example 10

Preparation of Filler B-3 (with Average Particle size of 20 μm)

The dried powder 3A was subjected to heat treatment in an electric furnace at 800° C. for one hour to obtain a spherical calcined amorphous powder having an average particle size of 20 μm. 100 g of the spherical calcined amorphous powder, 250 mL of toluene, and 30 g of 11-methacryloyloxyundecyl-trimethoxysilane were charged into a three-necked flask equipped with a reflux tube, and the mixture was heated and refluxed under stirring. Toluene was distilled off under reduced pressure, and then the residue was vacuum-dried at 40° C. for 16 hours, and further heated at 90° C. for 3 hours. Thus, a filler B-3 having an average particle size of 20 μm, in which surface-treated layers are formed, was obtained.

Preparation Example 11

Preparation of Filler B-4 (with Average Particle Size of 10 μm)

The dried powder 4A was subjected to heat treatment in an electric furnace at 800° C. for one hour to obtain an irregular-shaped calcined amorphous powder having an average particle size of 10 μm. 100 g of the irregular-shaped calcined amorphous powder, 250 mL of toluene, and 30 g of 11-methacryloyloxyundecyltrimethoxysilane were charged into a three-necked flask equipped with a reflux tube, and the mixture was heated and refluxed under stirring. Toluene was distilled off under reduced pressure, and then the residue was vacuum-dried at 40° C. for 16 hours, and further heated at 90° C. for 3 hours. Thus, a filler B-4 having an average particle size of 10 μm, in which surface-treated layers are formed, was obtained.

Preparation Example 12

Preparation of Filler B-5 (with Average Particle Size of 10 μm)

100 g of the dried powder 1A, 250 mL of toluene, and 30 g of 11-methacryloyloxyundecyltrimethoxysilane were charged into a three-necked flask equipped with a reflux tube, and the mixture was heated and refluxed under stirring. Toluene was distilled off under reduced pressure, and then the residue was vacuum-dried at 40° C. for 16 hours, and further heated at 90° C. for 3 hours. Thus, a filler B-5 having an average particle size of 10 μm, in which surface-treated layers are formed, was obtained.

Preparation Example 13

Preparation of Filler B-6 (with Average Particle Size of 25 μm)

The dried powder 5A was subjected to heat treatment in an electric furnace at 800° C. for one hour to obtain a spherical calcined amorphous powder having an average particle size of 25 μm. 100 g of the spherical calcined amorphous powder, 250 mL of toluene, and 30 g of 11-methacryloyloxyundecyl-trimethoxysilane were charged into a three-necked flask equipped with a reflux tube, and the mixture was heated and refluxed under stirring. Toluene was distilled off under reduced pressure, and then the residue was vacuum-dried at 40° C. for 16 hours, and further heated at 90° C. for 3 hours. Thus, a filler B-6 having an average particle size of 25 μm, in which surface-treated layers are formed, was obtained.

Preparation Example 14

Preparation of Filler B-7 (with Average Particle Size of 0.7 μm)

The dried powder 6A was subjected to heat treatment in an electric furnace at 800° C. for one hour to obtain a spherical calcined amorphous powder having an average particle size of 0.7 μm. 100 g of the spherical calcined amorphous powder, 250 mL of toluene, and 30 g of 11-methacryloyloxyundecyl-trimethoxysilane were charged into a three-necked flask equipped with a reflux tube, and the mixture was heated and refluxed under stirring. Toluene was distilled off under reduced pressure, and then the residue was vacuum-dried at 40° C. for 16 hours, and further heated at 90° C. for 3 hours. Thus, a filler B-7 having an average particle size of 0.7 μm, in which surface-treated layers are formed, was obtained.

Preparation Example 15

Preparation of Aggregated Silica-Zirconia Powder (Filler B-8 with Average Particle Size of 10 μm)

A pH-adjusted silica sol (with a pH of 2.5) prepared by adding dilute nitric acid to 147 g of a commercially available silica sol (Cataloid SI-30 having an average particle size of 10 to 14 nm, manufactured by Catalysts and Chemicals Industries Co. Ltd.), was added slowly dropwise to 85 g of zirconium acetate (zirconium acetate containing 15 to 16% Zr, manufactured by Sigma-Aldrich Corporation) to obtain a mixed sol. The mixed sol was dried in a spray dryer (manufactured by Fujisaki Electric Co., Ltd.) under the conditions of an inlet temperature of 200° C., an internal temperature of 70° C., and a liquid flow rate of 15 mL/min. The spherical powder thus obtained was dried by hot air at 200° C. for one hour. The dried amorphous powder further was dried in an electric furnace at 800° C. for one hour. Thus, a spherical calcined amorphous powder having an average particle size of 20 μm was obtained. 100 g of the spherical calcined amorphous powder, 250 mL of toluene, and 30 g of 11-methacryloyloxyundecyltrimethoxysilane were charged into a three-necked flask equipped with a reflux tube, and the mixture was heated and refluxed under stirring. Toluene was distilled off under reduced pressure, and then the residue was vacuum-dried at 40° C. for 16 hours, and further heated at 90° C. for 3 hours. Thus, a filler B-8 having an average particle size of 20 in which surface-treated layers are formed, was obtained.

Preparation Example 16

Preparation of Filler B-9 (with Average Particle Size of 10 μm)

The dried powder 1A was subjected to heat treatment in an electric furnace at 800° C. for one hour to obtain a spherical calcined amorphous powder having an average particle size of 10 μm. 100 g of the spherical calcined amorphous powder, 250 mL of toluene, and 30 g of 8-methacryloyloxyoctyltrimethoxysilane were charged into a three-necked flask equipped with a reflux tube, and the mixture was heated and refluxed under stirring. Toluene was distilled off under reduced pressure, and then the residue was vacuum-dried at 40° C. for 16 hours, and further heated at 90° C. for 3 hours. Thus, a filler B-9 having an average particle size of 10 μm, in which surface-treated layers are formed, was obtained.

Preparation Example 17

Preparation of Filler B-10 (with Average Particle Size of 10 μm)

The dried powder 1A was subjected to heat treatment in an electric furnace at 800° C. for one hour to obtain a spherical calcined amorphous powder having an average particle size of 10 μm. 100 g of the spherical calcined amorphous powder, 250 mL of toluene, and 30 g of 13-methacryloyloxytridecyl-trimethoxysilane were charged into a three-necked flask equipped with a reflux tube, and the mixture was heated and refluxed under stirring. Toluene was distilled off under reduced pressure, and then the residue was vacuum-dried at 40° C. for 16 hours, and further heated at 90° C. for 3 hours. Thus, a filler B-10 having an average particle size of 10 μm, in which surface-treated layers are formed, was obtained.

Preparation Example 18

Preparation of Filler B-11 (with Average Particle Size of 10 μm)

The dried powder 1A was subjected to heat treatment in an electric furnace at 400° C. for one hour to obtain a spherical calcined amorphous powder having an average particle size of 10 μm. 100 g of the spherical calcined amorphous powder, 250 mL of toluene, and 30 g of 11-methacryloyloxyundecyl-trimethoxysilane were charged into a three-necked flask equipped with a reflux tube, and the mixture was heated and refluxed under stirring. Toluene was distilled off under reduced pressure, and then the residue was vacuum-dried at 40° C. for 16 hours, and further heated at 90° C. for 3 hours. Thus, a filler B-11 having an average particle size of 10 μm, in which surface-treated layers are formed, was obtained.

Preparation Example 19

Preparation of Inorganic Particles C-1 (with Average Particle Size of 0.7 μm)

100 g of barium glass "UF 0.7" (manufactured by Schott), 4.0 g of 11-methacryloyloxyundecyltrimethoxysilane, and 200 mL of toluene were charged into a three-necked flask, and the mixture was stirred at room temperature for 2 hours. Toluene was distilled off under reduced pressure, and then the residue was vacuum-dried at 40° C. for 16 hours, and further heated at 90° C. for 3 hours. Thus, inorganic particles C-1 having an average particle size of 0.7 μm, in which surface-treated layers are formed, were obtained.

Preparation Example 20

Preparation of Inorganic Particles C-2 (with Average Particle Size of 0.4 μm)

100 g of barium glass "UF 0.4" (manufactured by Schott), 7.0 g of 11-methacryloyloxyundecyltrimethoxysilane, and 200 mL of toluene were charged into a three-necked flask, and the mixture was stirred at room temperature for 2 hours. Toluene was distilled off under reduced pressure, and then the residue was vacuum-dried at 40° C. for 16 hours, and further heated at 90° C. for 3 hours. Thus, inorganic particles C-2 having an average particle size of 0.4 μm, in which surface-treated layers are formed, were obtained.

Preparation Example 21

Preparation of Inorganic Particles C-3 (with Average Particle Size of 0.18 μm)

100 g of barium glass "GM27884 NanoFine 180 (having a particle size ranging from 0.05 to 0.5 μm and an average particle size of 0.18 μm)" (manufactured by Schott), 10 g of γ-methacryloxypropyltrimethoxysilane, and 200 mL of toluene were charged into a three-necked flask, and the mixture was stirred at room temperature for 2 hours. Toluene was distilled off under reduced pressure, and then the residue was vacuum-dried at 40° C. for 16 hours, and further heated at 90° C. for 3 hours. Thus, inorganic particles C-3 having an average particle size of 0.18 μM, in which surface-treated layers are formed, were obtained.

Preparation Example 22

Preparation of Inorganic Ultrafine Particles D-1 (with Average Particle Size of 0.02 μm)

100 g of nearly spherical inorganic ultrafine particles having an average particle size of 0.02 μM ("Ar 130" silica, manufactured by Nippon Aerosil Corporation), 40 g of 3-methacryloyloxypropyltrimethoxysilane, and 610 mL of toluene were charged into a flask, and the mixture was stirred vigorously at 30° C. for 20 minutes. Toluene was distilled off at 30° C. under reduced pressure, and the residue was vacuum-dried. Thus, inorganic ultrafine particles D-1 having an average particle size of 0.02 μm, in which surface-treated layers are formed, were obtained.

Preparation Example 23

Preparation of Inorganic Ultrafine Particles D-2 (with Average Particle Size of 0.02 μm)

100 g of nearly spherical inorganic ultrafine particles having an average particle size of 0.02 μm ("Aeroxide AluC"

alumina, manufactured by Nippon Aerosil Corporation), 20 g of 3-methacryloyloxypropyltrimethoxysilane, and 610 mL of toluene were charged into a flask, and the mixture was stirred vigorously at 30° C. for 20 minutes. Toluene was distilled off at 30° C. under reduced pressure, and the residue was vacuum-dried. Thus, inorganic ultrafine particles D-2 having an average particle size of 0.02 μm, in which surface-treated layers are formed, were obtained.

Preparation Example 24

Preparation of Inorganic Ultrafine Particles D-3 (with Average Particle Size of 0.007 μm)

100 g of nearly spherical inorganic ultrafine particles having an average particle size of 0.007 μm ("Ar 380" silica, manufactured by Nippon Aerosil Corporation), 50 g of 3-methacryloyloxypropyltrimethoxysilane, and 900 mL of toluene were charged into a flask, and the mixture was stirred vigorously at 30° C. for 20 minutes. Toluene was distilled off at 30° C. under reduced pressure, and the residue was vacuum-dried. Thus, inorganic ultrafine particles D-3 having an average particle size of 0.007 μm, in which surface-treated layers are formed, were obtained.

Preparation Example 25

Preparation of Inorganic Ultrafine Particles D-4 (with Average Particle Size of 0.04 μm)

100 g of nearly spherical inorganic ultrafine particles having an average particle size of 0.04 μm ("OX 50" silica, manufactured by Nippon Aerosil Corporation), 10 g of 3-methacryloyloxypropyltrimethoxysilane, and 500 mL of toluene were charged into a flask, and the mixture was stirred vigorously at 30° C. for 20 minutes. Toluene was distilled off at 30° C. under reduced pressure, and the residue was vacuum-dried. Thus, inorganic ultrafine particles D-4 having an average particle size of 0.04 μm, in which surface-treated layers are formed, were obtained.

Preparation Example 26

Preparation of Polymerizable Monomer Component (A)

The polymerizable monomer component (A) was prepared according to the formulations shown in Table 1 or Table 2. 100 parts by weight of the polymerizable monomer component (A), 0.3 part by weight of camphorquinone, 1.2 parts by weight of ethyl N,N-dimethylaminobenzoate, and 0.05 part by weight of butylhydroxytoluene (BHT) were mixed, and a polymerizable monomer composition was obtained.

Examples 1 to 48 and Comparative Examples 1 to 5

As shown in Tables 1 to 5, the filler (B), the inorganic particles (C), the inorganic ultrafine particles (D), and the polymerizable monomer component (A) (polymerizable monomer composition) were mixed. As a result, dental composition pastes of Examples 1 to 48 and Comparative Examples 1 to 5 were prepared. In each of Examples 1 to 48 and Comparative Examples 1 to 5, the forming property, consistency, viscosity, flexural strength, and surface smoothness and gloss were evaluated by the methods described above.

TABLE 1

|  |  |  | Examples |  |  |  |  |  |  |  |  |  |  |  |  |  |
|---|---|---|---|---|---|---|---|---|---|---|---|---|---|---|---|---|
|  |  |  | 1 | 2 | 3 | 4 | 5 | 6 | 7 | 8 | 9 | 10 | 11 | 12 | 13 | 14 |
| Components of dental composition | Filler (B) | B-1 | 450 | 150 | 350 | 250 | 50 | 250 | 250 | — | — | — | — | 250 | 450 | 450 |
|  |  | B-2 | — | — | — | — | — | — | — | 450 | — | — | — | — | — | — |
|  |  | B-3 | — | — | — | — | — | — | — | — | 450 | — | — | — | — | — |
|  |  | B-4 | — | — | — | — | — | — | — | — | — | 450 | — | — | — | — |
|  |  | B-5 | — | — | — | — | — | — | — | — | — | — | 450 | — | — | — |
|  | Inorganic particles (C) | C-1 | — | — | 100 | 200 | 400 | 150 | 180 | — | — | — | — | — | — | — |
|  |  | C-2 | — | — | — | — | — | — | — | — | — | — | — | 200 | — | — |
|  | Inorganic fine particles (D) | D-1 | — | — | — | — | — | 50 | 20 | — | — | — | — | — | — | — |
|  | Polymerizable monomer component (A) | D2.6E | 75 | 75 | 75 | 75 | 75 | 75 | 75 | 75 | 75 | 75 | 75 | 75 | 35 | — |
|  |  | Bis-GMA | — | — | — | — | — | — | — | — | — | — | — | — | 45 | — |
|  |  | UDMA | — | — | — | — | — | — | — | — | — | — | — | — | — | 75 |
|  |  | 3G | 25 | 25 | 25 | 25 | 25 | 25 | 25 | 25 | 25 | 25 | 25 | 25 | 20 | 25 |
| Physical properties | Forming property |  | 4 | 5 | 4 | 3 | 3 | 2 | 2 | 3 | 4 | 2 | 4 | 3 | 4 | 3 |
|  | Consistency (mm) |  | 34 | 39 | 32 | 29 | 24 | 26 | 30 | 28 | 36 | 23 | 33 | 26 | 36 | 34 |
|  | Viscosity of composition (Pa·s) |  | 125 | 45 | 117 | 280 | 400 | 350 | 230 | 400 | 89 | 740 | 128 | 360 | 150 | 134 |
|  | Flexural strength (MPa) |  | 145 | 132 | 150 | 152 | 165 | 140 | 152 | 135 | 150 | 156 | 138 | 148 | 148 | 141 |
|  | Surface smoothness and gloss |  | A | A | B | B | B | B | B | A | A | A | A | A | A | A |

* The amounts of components of each composition are represented by parts by weight.

* Polymerizable monomer component . . . D2.6E: 2,2-bis[4-(meth)acryloyloxypolyethoxyphenyl]propane, Bis-GMA: 2,2-bis[4-[3-(meth)acryloyloxy-2-hydroxypropoxy]phenyl]propane, UDMA: N,N'-(2,2,4-trimethylhexamethylene)bis(2-(aminocarboxy)ethane-1-ol)dimethacrylate, 3G: triethylene glycol di(meth)acrylate

TABLE 2

| | | | Examples | | | | | | | | | | | | | |
|---|---|---|---|---|---|---|---|---|---|---|---|---|---|---|---|---|
| | | | 15 | 16 | 17 | 18 | 19 | 20 | 21 | 22 | 23 | 24 | 25 | 26 | 27 | 28 | 29 |
| Components of dental composition | Filler (B) | B-1 | 350 | 450 | 400 | 400 | 400 | 250 | 450 | 290 | 250 | — | — | — | — | — | — |
| | | B-4 | — | — | — | — | — | — | — | 160 | 100 | — | — | — | — | — | — |
| | | B-9 | — | — | — | — | — | — | — | — | — | 400 | 400 | — | — | — | — |
| | | B-10 | — | — | — | — | — | — | — | — | — | — | — | 400 | 400 | — | — |
| | | B-11 | — | — | — | — | — | — | — | — | — | — | — | — | — | 350 | 350 |
| | Inorganic particles (C) | C-1 | — | — | — | — | — | — | — | — | — | — | — | — | — | — | — |
| | | C-2 | — | — | — | — | — | — | — | — | — | — | — | — | — | — | — |
| | Inorganic fine particles (D) | D-1 | 100 | 5 | 10 | 50 | — | — | — | — | 20 | — | 20 | — | 25 | — | 20 |
| | | D-2 | — | — | — | — | 20 | — | — | — | — | — | — | — | — | — | — |
| | | D-3 | — | — | — | — | — | 40 | — | — | — | — | — | — | — | — | — |
| | | D-4 | — | — | — | — | — | — | 20 | — | — | — | — | — | — | — | — |
| | Polymerizable monomer component (A) | D2.6E | 75 | 75 | 75 | 75 | 75 | 75 | 75 | 75 | 75 | 75 | 75 | 75 | 75 | 75 | 75 |
| | | Bis-GMA | — | — | — | — | — | — | — | — | — | — | — | — | — | — | — |
| | | UDMA | — | — | — | — | — | — | — | — | — | — | — | — | — | — | — |
| | | 3G | 25 | 25 | 25 | 25 | 25 | 25 | 25 | 25 | 25 | 25 | 25 | 25 | 25 | 25 | 25 |
| Physical properties | Forming property | | 2 | 4 | 4 | 3 | 4 | 3 | 4 | 3 | 4 | 4 | 3 | 4 | 3 | 3 | 2 |
| | Consistency (mm) | | 23 | 32 | 34 | 30 | 31 | 27 | 36 | 31 | 35 | 36 | 34 | 39 | 33 | 32 | 26 |
| | Viscosity of composition (Pa·s) | | 700 | 136 | 145 | 220 | 140 | 402 | 130 | 205 | 142 | 140 | 146 | 51 | 131 | 210 | 543 |
| | Flexural strength (MPa) | | 136 | 145 | 141 | 143 | 139 | 131 | 149 | 150 | 140 | 140 | 142 | 136 | 141 | 133 | 138 |
| | Surface smoothness and gloss | | A | A | A | A | A | A | A | A | A | A | A | A | A | A | A |

\* The amounts of components of each composition are represented by parts by weight.
\* Polymerizable monomer component . . . D2.6E: 2,2-bis[4-(meth)acryloyloxypolyethoxyphenyl]propane, Bis-GMA: 2,2-bis[4-[3-(meth)acryloyloxy-2-hydroxypropoxy]phenyl]propane, UDMA: N,N'-(2,2,4-trimethylhexamethylene)bis(2-(aminocarboxy)ethane-1-ol)dimethacrylate, 3G: triethylene glycol di(meth)acrylate

TABLE 3

| | | | Examples | | | | | | | | | | | | | |
|---|---|---|---|---|---|---|---|---|---|---|---|---|---|---|---|---|
| | | | 30 | 31 | 32 | 33 | 34 | 35 | 36 | 37 | 38 | 39 | 40 | 41 | 42 | 43 |
| Components of dental composition | Filler (B) | B-1 | — | — | — | — | 400 | 400 | 400 | 400 | 200 | 200 | 200 | 150 | 175 | 200 |
| | | B-2 | 400 | — | — | — | — | — | — | — | — | — | — | — | — | — |
| | | B-3 | — | 400 | — | — | — | — | — | — | — | — | — | — | — | — |
| | | B-4 | — | — | 400 | — | — | — | — | — | — | — | — | 50 | 125 | 50 |
| | | B-5 | — | — | — | 400 | — | — | — | — | — | — | — | — | — | — |
| | Inorganic particles (C) | C-1 | — | — | — | — | — | — | — | — | 150 | 150 | — | 100 | 50 | — |
| | | C-2 | — | — | — | — | — | — | — | — | — | — | 125 | — | — | 50 |
| | Inorganic fine particles (D) | D-1 | 20 | 20 | 20 | 20 | 20 | 20 | — | — | — | — | — | 20 | 20 | 20 |
| | | D-2 | — | — | — | — | — | — | 20 | 20 | 20 | — | — | — | — | — |
| | | D-3 | — | — | — | — | — | — | — | — | — | 20 | — | — | — | — |
| | | D-4 | — | — | — | — | — | — | — | — | — | — | 20 | — | — | — |
| | Polymerizable monomer component (A) | D2.6E | 75 | 75 | 75 | 75 | 35 | — | 35 | — | 75 | 75 | 75 | 75 | 75 | 75 |
| | | Bis-GMA | — | — | — | — | 45 | — | 45 | — | — | — | — | — | — | — |
| | | UDMA | — | — | — | — | — | 75 | — | 75 | — | — | — | — | — | — |
| | | 3G | 25 | 25 | 25 | 25 | 20 | 25 | 20 | 25 | 25 | 25 | 25 | 25 | 25 | 25 |
| Physical properties | Forming property | | 3 | 4 | 2 | 4 | 4 | 3 | 3 | 3 | 3 | 2 | 4 | 3 | 3 | 3 |
| | Consistency (mm) | | 29 | 36 | 22 | 34 | 32 | 30 | 31 | 28 | 31 | 24 | 33 | 36 | 31 | 29 |
| | Viscosity of composition (Pa·s) | | 386 | 97 | 768 | 121 | 171 | 381 | 207 | 406 | 197 | 531 | 167 | 107 | 216 | 393 |
| | Flexural strength (MPa) | | 141 | 140 | 157 | 134 | 150 | 136 | 147 | 139 | 154 | 148 | 160 | 153 | 150 | 142 |
| | Surface smoothness and gloss | | A | A | A | A | A | A | A | A | B | B | B | B | B | B |

\* The amounts of components of each composition are represented by parts by weight.
\* Polymerizable monomer component . . . D2.6E: 2,2-bis[4-(meth)acryloyloxypolyethoxyphenyl]propane, Bis-GMA: 2,2-bis[4-[3-(meth)acryloyloxy-2-hydroxypropoxy]phenyl]propane, UDMA: N,N'-(2,2,4-trimethylhexamethylene)bis(2-(aminocarboxy)ethane-1-ol)dimethacrylate, 3G: triethylene glycol di(meth)acrylate

TABLE 4

|  |  |  | Examples | | | | |
| --- | --- | --- | --- | --- | --- | --- | --- |
|  |  |  | 44 | 45 | 46 | 47 | 48 |
| Components of dental composition | Filler (B) | B-1 | 350 |  | 200 |  |  |
|  |  | B-2 |  | 350 |  | 200 |  |
|  |  | B-3 |  |  |  |  |  |
|  |  | B-4 |  |  |  |  | 200 |
|  |  | B-5 |  |  |  |  |  |
|  | Inorganic particles (C) | C-1 |  |  |  |  |  |
|  |  | C-2 |  |  |  |  |  |
|  |  | C-3 | 100 | 100 | 150 | 150 | 150 |
|  | Inorganic fine particles (D) | D-1 |  |  | 20 |  | 20 |
|  |  | D-2 |  |  |  |  |  |
|  |  | D-3 |  |  |  | 20 |  |
|  |  | D-4 |  |  |  |  |  |
|  | Polymerizable monomer component (A) | D2.6E | 75 | 75 | 75 | 75 | 75 |
|  |  | Bis-GMA |  |  |  |  |  |
|  |  | UDMA |  |  |  |  |  |
|  |  | 3G | 25 | 25 | 25 | 25 | 25 |
| Physical properties | Forming property |  | 3 | 3 | 3 | 3 | 3 |
|  | Consistency (mm) |  | 30 | 31 | 29 | 32 | 28 |
|  | Viscosity of composition (Pa · s) |  | 261 | 280 | 278 | 249 | 361 |
|  | Flexural strength (MPa) |  | 146 | 143 | 147 | 148 | 150 |
|  | Surface smoothness and gloss |  | A | A | B | B | B |

* The amounts of components of each composition are represented by parts by weight.
* Polymerizable monomer component . . . D2.6E: 2,2-bis[4-(meth)acryloyloxypolyethoxyphenyl]propane, Bis-GMA: 2,2-bis[4-[3-(meth)acryloyloxy-2-hydroxypropoxy]phenyl]propane, UDMA: N,N'-(2,2,4-trimethylhexamethylene)bis(2-(aminocarboxy)ethane-1-ol)dimethacrylate,

TABLE 5

|  |  |  | Comparative Examples | | | | |
| --- | --- | --- | --- | --- | --- | --- | --- |
|  |  |  | 1 | 2 | 3 | 4 | 5 |
| Components of dental composition | Filler (B) | B-1 | — | 600 | — | — | — |
|  |  | B-6 | — | — | 450 | — | — |
|  |  | B-7 | — | — | — | 450 | — |
|  |  | B-8 | — | — | — | — | 450 |
|  | Inorganic particles (C) | C-1 | 500 | — | — | — | — |
|  |  | C-2 | — | — | — | — | — |
|  | Inorganic ultrafine particles (D) | D-1 | — | — | — | — | — |
|  | Polymerizable monomer component (A) | D2.6E | 75 | 75 | 75 | 75 | 75 |
|  |  | Bis-GMA | — | — | — | — | — |
|  |  | UDMA | — | — | — | — | — |
|  |  | 3G | 25 | 25 | 25 | 25 | 25 |
| Physical properties | Forming property |  | 1 | 1 | 6 | 1 | 4 |
|  | Consistency (mm) |  | 22 | 20 | 48 | 19 | 36 |
|  | Viscosity of composition (Pa · s) |  | 860 | 900 | 40 | 970 | 153 |
|  | Flexural strength (MPa) |  | 165 | 175 | 150 | 120 | 115 |
|  | Surface smoothness and gloss |  | B | A | A | A | A |

* The amounts of components of each composition are represented by parts by weight.
* Polymerizable monomer component . . . D2.6E: 2,2-bis[4-(meth)acryloyloxypolyethoxyphenyl]propane, Bis-GMA: 2,2-bis[4-[3-(meth)acryloyloxy-2-hydroxypropoxy]phenyl]propane, UDMA: N,N'-(2,2,4-trimethylhexamethylene)bis(2-(aminocarboxy)ethane-1-ol)dimethacrylate, 3G: triethylene glycol di(meth)acrylate These results show the following. Each of the dental compositions of Examples 1 to 48 contains the polymerizable monomer component (A), and a specific amount of the amorphous filler (B) having an average particle size of 1 to 20 µm. This amorphous filler (B) includes silica-based fine particles and coatings of an oxide that cover the surfaces of the silica-based fine particles, and the oxide contains at least zirconium, silicon, and oxygen. The viscosity of the dental composition is in a specific range defined in the present invention. These dental compositions of Examples each have good consistency and forming property as a paste which has not yet been polymerized, and further have excellent flexural strength and surface smoothness and gloss as a cured product, compared with the dental compositions of Comparative Examples.

The comparison between Example 1 and Example 10 shows that the use of the spherical filler (B) decreases the paste viscosity while maintaining the same level of strength. It is clear from the comparison between Example 1 and Example 11 that the strength increases when the filler (B) is calcined. The comparison among Examples 1, and 3 to 5 shows that the addition of the inorganic particles (C) having a relatively large particle size further increases the strength.

The comparison among Examples 1, 6, and 7 shows that the addition of the inorganic ultrafine particles (D) having a small particle size improves the forming property of the paste. The comparison among Examples 1, 13, and 14 shows that the use of the special filler (B) defined in the present invention provides the dental composition with appropriate viscosity and strength, regardless of the viscosity of the polymerizable monomer component (A) used.

On the other hand, the results of Comparative Example 1 show that when only the inorganic particles (C) are used to achieve the same level of strength as those in Examples 1 to 48, the paste has an increased viscosity, which is not suitable for the paste to be used as a direct-filling treatment material. The results of Comparative Example 2 show that when a predetermined amount or more of the filler (B) is contained, the strength increases but the viscosity may not be suitable for the paste to be used as a direct-filling treatment material in some cases. The results of Comparative Examples 3 and 4 show that when the particle size of the spherical amorphous powder is out of the specific range, desired paste properties cannot be obtained. The results of Comparative Example 5 show that the dental composition using an aggregated silica-zirconia powder not having a specific structure is inferior in mechanical strength.

INDUSTRIAL APPLICABILITY

The dental composition of the present invention can be used suitably as a substitute for a part of a natural tooth or an entire natural tooth in the field of dental treatment.

The invention claimed is:

1. A dental composition comprising:
a polymerizable monomer component (A);
20 to 500 parts by weight of an amorphous filler (B) per 100 parts by weight of the polymerizable monomer component (A), said amorphous filler having an average particle size of 1 to 20 μm and comprising silica-based fine particles and coatings of an oxide that cover the surfaces of the silica-based fine particles, the oxide comprising a zirconium atom, a silicon atom, and an oxygen atom, and
inorganic ultrafine particles (D) having an average particle size of from 5 to 50 nm,
wherein
the oxide coatings cover a plurality of the silica-based fine particles,
filler (B) has a structure in which the oxide coating of the silica-based fine particle and the oxide coating of a neighboring silica-based fine particle extend and are connected to each other, and
the dental composition has a viscosity of 10 to 800 Pa·s.

2. The dental composition according to claim 1, wherein the filler (B) comprises spherical particles, and the percentage of the spherical particles in the filler (B) is at least 60%.

3. The dental composition according to claim 2, wherein the filler (B) consists of the spherical particles.

4. The dental composition according to claim 2, wherein the filler (B) comprises particles obtained by a process comprising spray-drying a mixed liquid comprising ultrafine particles that are silica-based fine particles whose surfaces are covered with coatings of an oxide comprising at least a zirconium atom, a silicon atom, and an oxygen atom.

5. The dental composition according to claim 1, further comprising inorganic particles (C) having an average particle size of from 0.1 to 1.0 μm,
wherein the dental composition comprises 50 to 400 parts by weight of the inorganic particles (C) per 100 parts by weight of the polymerizable monomer component (A).

6. The dental composition according to claim 5, wherein the inorganic particles (C) comprise silica as a main component.

7. The dental composition according to claim 1, wherein the average particle size of the inorganic ultrafine particles (D) is 10 to 40 nm.

8. The dental composition according to claim 1, wherein the dental composition comprises 10 to 50 parts by weight of the inorganic ultrafine particles (D) per 100 parts by weight of the polymerizable monomer component (A).

9. The dental composition according to claim 1, wherein the silica-based fine particles have an average particle size of from 2 to 300 nm.

10. The dental composition according to claim 1, wherein in the filler (B), the oxide coating covers each of the silica-based fine particles.

11. The dental composition according to claim 1, wherein the filler (B) has a structure in which the oxide coating of the silica-based fine particle and the oxide coating of a plurality of neighboring silica-based fine particles extend and are connected to each other.

12. The dental composition according to claim 1, wherein the filler (B) has a porous particle structure in which the oxide coatings are connected to each other to form an aggregate of the silica-based fine particles covered with the oxide coatings.

13. The dental composition according to claim 1, wherein the filler (B) is a calcined product.

14. The dental composition according to claim 1, wherein the filler (B) further comprises, on the oxide coating, a surface-treated layer of at least one organic metal compound selected from the group consisting of an organic silicon compound, an organic titanium compound, an organic zirconium compound, and an organic aluminum compound.

15. A composite resin comprising the dental composition according to claim 1.

16. The dental composition according to claim 11, wherein the filler (B) has a porous particle structure in which the oxide coatings are connected to each other to form an aggregate of the silica-based fine particles covered with the oxide coatings.

17. The dental composition according to claim 11, wherein the filler (B) has a tetrapod or a star structure.

18. The dental composition according to claim 1, wherein polymerizable monomer component (A) comprises an aromatic polymerizable monomer (a) having a hydroxyl group, an aromatic polymerizable monomer (b) not having a hydroxyl group, and an aliphatic polymerizable monomer (c).

19. The dental composition according to claim 11, wherein polymerizable monomer component (A) comprises an aromatic polymerizable monomer (a) having a hydroxyl group, an aromatic polymerizable monomer (b) not having a hydroxyl group, and an aliphatic polymerizable monomer (c).

20. The dental composition according to claim 19, wherein the average particle size of the inorganic ultrafine particles (D) is 10 to 40 nm.

* * * * *